US011911398B2

(12) United States Patent
Bishop et al.

(10) Patent No.: US 11,911,398 B2
(45) Date of Patent: *Feb. 27, 2024

(54) TREATING VITAMIN D INSUFFICIENCY AND DEFICIENCY WITH 25-HYDROXYVITAMIN $D_2$ AND 25-HYDROXYVITAMIN $D_3$

(71) Applicant: OPKO RENAL, LLC, Miami, FL (US)

(72) Inventors: Charles W. Bishop, Miami, FL (US); Keith H. Crawford, Parker, CO (US); Eric J. Messner, Lake Forest, IL (US)

(73) Assignee: OPKO RENAL, LLC, Miami, FL (US)

(*) Notice: Subject to any disclaimer, the term of this patent is extended or adjusted under 35 U.S.C. 154(b) by 350 days.

This patent is subject to a terminal disclaimer.

(21) Appl. No.: 17/237,889

(22) Filed: Apr. 22, 2021

(65) Prior Publication Data
US 2021/0236517 A1 Aug. 5, 2021

Related U.S. Application Data

(60) Continuation of application No. 16/171,100, filed on Oct. 25, 2018, now Pat. No. 11,007,204, which is a continuation of application No. 15/722,757, filed on Oct. 2, 2017, now Pat. No. 10,213,442, which is a continuation of application No. 14/548,275, filed on Nov. 19, 2014, now Pat. No. 9,943,530, which is a continuation of application No. 13/848,982, filed on Mar. 22, 2013, now Pat. No. 8,906,410, which is a division of application No. 12/278,053, filed as application No. PCT/US2007/061521 on Feb. 2, 2007, now Pat. No. 8,426,391.

(60) Provisional application No. 60/764,665, filed on Feb. 3, 2006.

(51) Int. Cl.
A61K 31/593 (2006.01)
A61K 9/00 (2006.01)
A61K 9/48 (2006.01)
A61K 31/592 (2006.01)
A61K 9/16 (2006.01)
A61K 47/26 (2006.01)

(52) U.S. Cl.
CPC ............. *A61K 31/593* (2013.01); *A61K 9/00* (2013.01); *A61K 9/0019* (2013.01); *A61K 9/16* (2013.01); *A61K 9/48* (2013.01); *A61K 9/4808* (2013.01); *A61K 9/4858* (2013.01); *A61K 9/4866* (2013.01); *A61K 9/4875* (2013.01); *A61K 31/592* (2013.01); *A61K 47/26* (2013.01)

(58) Field of Classification Search
CPC ...... A61K 31/593; A61K 9/00; A61K 9/0019; A61K 9/48; A61K 9/4858; A61K 31/592
See application file for complete search history.

(56) References Cited

U.S. PATENT DOCUMENTS

| | | |
|---|---|---|
| 3,565,924 A | 2/1971 | DeLuca et al. |
| 3,833,622 A | 9/1974 | Babcock et al. |
| 3,880,894 A | 4/1975 | De Luca et al. |
| 3,974,272 A | 8/1976 | Polli et al. |
| 4,004,003 A | 1/1977 | Babcock et al. |
| 4,230,701 A | 10/1980 | Holick et al. |
| 4,335,120 A | 6/1982 | Holick et al. |
| 4,442,093 A | 4/1984 | Maeda et al. |
| 4,448,721 A | 5/1984 | DeLuca et al. |
| 4,555,364 A | 11/1985 | DeLuca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |
| 4,729,895 A | 3/1988 | Makino et al. |
| 4,755,544 A | 7/1988 | Makino et al. |
| 4,892,821 A | 1/1990 | Omura et al. |
| 4,997,824 A | 3/1991 | Popovtzer et al. |

(Continued)

FOREIGN PATENT DOCUMENTS

| | | |
|---|---|---|
| CA | 2241205 A1 | 7/1997 |
| CN | 101668517 A | 3/2010 |

(Continued)

OTHER PUBLICATIONS

English translation of WO0212182 (Year: 2002).*
Hidroferol® (calcifediol): Casos de Hipercalcemia e Hipervitaminosis D, Butlletí de Farmacovigilància de Catalunya, 9(5):17-20 (2011).
K/DOQI Clinical Practice Guidelines for Bone Metabolism and Disease in Chronic Kidney Disease, National Kidney Foundation, Am. J. Kidney Dis., 42 (Supplement 3):1-202 (2003).
Modern Pharmaceutics 4th ed., Marcel Dekker, Inc., New York, NY, p. 16-21 (2002).
Al-Aly, Z., Changes in Serum 25-Hydroxyvitamin D and Plasma Intact PTH Levels Following Treatment with Ergocalciferol in Patients With CKD, Am. J. Kid. Dis., 50(1):59-68 (2007).
AlfaD3® 0.25, 0.5 or 1 microgram Capsules (Alfacalcidol, Package Leaflet, Apr. 2010).
Alfarol® Capsules 3 μg (Package Leaflet, Mar. 2011).
Alvarez et al., Vitamin D Supplementation in Pre-Dialysis Chronic Kidney Disease, Dermato-Endocrinology, 4(2):118-127 (2012).
Andress, Vitamin D in chronic kidney disease: A systematic role for selective vitamin D receptor activation, Kidney Int., 69:33-43 (2006).

(Continued)

*Primary Examiner* — San Ming R Hui
(74) *Attorney, Agent, or Firm* — MARSHALL, GERSTEIN & BORUN LLP

(57) ABSTRACT

Methods and compositions for treating 25-hydroxyvitamin D insufficiency and deficiency in a patient are described herein. The method includes orally administering to the patient a delayed, sustained release formulation including a first ingredient selected from the group consisting of 25-hydroxyvitamin $D_2$, 25-hydroxyvitamin $D_3$, or a combination of 25-hydroxyvitamin $D_2$ and 25-hydroxyvitamin $D_3$, or it includes gradually administering to the patient a sterile intravenous formulation including a first ingredient selected from the group consisting of 25-hydroxyvitamin $D_2$, 25-hydroxyvitamin $D_3$, or a combination of 25-hydroxyvitamin $D_2$ and 25-hydroxyvitamin $D_3$.

20 Claims, No Drawings

(56) References Cited

U.S. PATENT DOCUMENTS

| | | |
|---|---|---|
| 5,026,559 A | 6/1991 | Eichel et al. |
| 5,160,742 A | 11/1992 | Mazer et al. |
| 5,167,965 A | 12/1992 | Schulz |
| 5,328,903 A | 7/1994 | Ishii et al. |
| 5,342,626 A | 8/1994 | Winston, Jr. et al. |
| 5,354,743 A | 10/1994 | Thys-Jacobs |
| 5,403,831 A | 4/1995 | DeLuca et al. |
| 5,431,917 A | 7/1995 | Yamamoto et al. |
| 5,472,712 A | 12/1995 | Oshlack et al. |
| 5,487,900 A | 1/1996 | Itoh et al. |
| 5,529,991 A | 6/1996 | Knutson et al. |
| 5,593,690 A | 1/1997 | Akiyama et al. |
| 5,602,116 A | 2/1997 | Knutson et al. |
| 5,614,513 A | 3/1997 | Knutson et al. |
| 5,622,941 A | 4/1997 | Knutson et al. |
| 5,693,615 A | 12/1997 | Stone |
| 5,707,980 A | 1/1998 | Knutson et al. |
| 5,756,123 A | 5/1998 | Yamamoto et al. |
| 5,783,215 A | 7/1998 | Arwidsson et al. |
| 5,795,882 A | 8/1998 | Bishop et al. |
| 5,861,386 A | 1/1999 | Knutson et al. |
| 5,869,473 A | 2/1999 | Knutson et al. |
| 5,872,113 A | 2/1999 | Nestor, Jr. et al. |
| 5,888,994 A | 3/1999 | Hennessy et al. |
| 5,919,986 A | 7/1999 | Barbier et al. |
| 5,939,408 A | 8/1999 | Batcho et al. |
| 5,958,451 A | 9/1999 | Chen |
| 5,976,784 A | 11/1999 | DeLuca et al. |
| 6,001,884 A | 12/1999 | Nemeth et al. |
| 6,011,068 A | 1/2000 | Nemeth et al. |
| 6,031,003 A | 2/2000 | Nemeth et al. |
| 6,034,075 A | 3/2000 | Thys-Jacobs |
| 6,051,567 A | 4/2000 | Abrahamson et al. |
| 6,096,876 A | 8/2000 | St-Arnaud et al. |
| 6,121,469 A | 9/2000 | Norman et al. |
| 6,133,250 A | 10/2000 | Knutson et al. |
| 6,139,875 A | 10/2000 | Adams et al. |
| 6,147,064 A | 11/2000 | Knutson et al. |
| 6,150,346 A | 11/2000 | Knutson et al. |
| 6,190,591 B1 | 2/2001 | van Lengerich |
| 6,190,695 B1 | 2/2001 | Hoshino et al. |
| 6,211,244 B1 | 4/2001 | Van Wagenen et al. |
| 6,214,376 B1 | 4/2001 | Gennadios |
| 6,228,849 B1 | 5/2001 | Thys-Jacobs |
| 6,242,434 B1 | 6/2001 | Bishop et al. |
| 6,265,392 B1 | 7/2001 | Abrahamson et al. |
| 6,274,169 B1 | 8/2001 | Abrahamson et al. |
| 6,288,849 B1 | 9/2001 | Teramoto |
| 6,313,146 B1 | 11/2001 | Van Wagenen et al. |
| 6,340,473 B1 | 1/2002 | Tanner et al. |
| 6,342,249 B1 | 1/2002 | Wong et al. |
| 6,375,981 B1 | 4/2002 | Gilleland et al. |
| 6,376,479 B1 | 4/2002 | Knutson et al. |
| 6,380,408 B1 | 4/2002 | Posner et al. |
| 6,413,463 B1 | 7/2002 | Yamamoto et al. |
| 6,432,936 B1 | 8/2002 | DeLuca et al. |
| 6,491,950 B1 | 12/2002 | Gutierrez-Rocca et al. |
| 6,503,893 B2 | 1/2003 | Bishop et al. |
| 6,521,608 B1 | 2/2003 | Henner et al. |
| 6,524,788 B1 | 2/2003 | Cantor |
| 6,569,463 B2 | 5/2003 | Patel et al. |
| 6,572,888 B2 | 6/2003 | Byrd |
| 6,582,727 B2 | 6/2003 | Tanner et al. |
| 6,596,314 B2 | 7/2003 | Wong et al. |
| 6,627,622 B2 | 9/2003 | DeLuca et al. |
| 6,645,527 B2 | 11/2003 | Oshlack et al. |
| 6,770,295 B1 | 8/2004 | Kreilg et al. |
| 6,887,493 B2 | 5/2005 | Shefer et al. |
| 6,893,658 B1 | 5/2005 | Iida et al. |
| 6,903,083 B2 | 6/2005 | Knutson et al. |
| 6,911,217 B1 | 6/2005 | Gren et al. |
| 6,923,988 B2 | 8/2005 | Patel et al. |
| 6,929,803 B2 | 8/2005 | Wong et al. |
| 6,949,256 B2 | 9/2005 | Fonkwe et al. |
| 6,982,258 B2 | 1/2006 | Posner et al. |
| RE39,079 E | 4/2006 | Tanner et al. |
| 7,033,996 B2 | 4/2006 | Christakos |
| 7,056,655 B2 | 6/2006 | Cantor |
| 7,101,865 B2 | 9/2006 | Posner et al. |
| 7,122,530 B2 | 10/2006 | Bishop et al. |
| 7,166,585 B2 | 1/2007 | Posner et al. |
| 7,189,843 B2 | 3/2007 | Tsai et al. |
| 7,226,932 B2 | 6/2007 | Gokhale et al. |
| 7,255,921 B2 | 8/2007 | Kamaguchi et al. |
| 7,422,758 B2 | 9/2008 | Block et al. |
| 7,528,122 B2 | 5/2009 | DeLuca et al. |
| 7,632,518 B2 | 12/2009 | Tritsch et al. |
| 7,648,826 B1 | 1/2010 | Albertson et al. |
| 7,807,194 B2 | 10/2010 | Modliszewski et al. |
| 7,816,341 B2 | 10/2010 | Sewall et al. |
| 7,829,595 B2 | 11/2010 | Lawrence et al. |
| 7,846,475 B2 | 12/2010 | Shiraishi et al. |
| 7,973,024 B2 | 7/2011 | Posner et al. |
| 8,088,410 B2 | 1/2012 | Tritsch et al. |
| 8,101,203 B2 | 1/2012 | Cao |
| 8,101,204 B2 | 1/2012 | Cao |
| 8,142,811 B2 | 3/2012 | Oshlack et al. |
| 8,207,149 B2 | 6/2012 | Tabash et al. |
| 8,231,896 B2 | 7/2012 | Tanner et al. |
| 8,268,352 B2 | 9/2012 | Vaya et al. |
| 8,293,270 B2 | 10/2012 | Sukuru |
| 8,329,677 B2 | 12/2012 | Bishop et al. |
| 8,361,488 B2 | 1/2013 | Bishop et al. |
| 8,377,470 B2 | 2/2013 | Tanner et al. |
| 8,426,391 B2 | 4/2013 | Bishop et al. |
| 8,592,401 B2 | 11/2013 | Petkovich et al. |
| 8,759,328 B2 | 6/2014 | Deluca et al. |
| 8,778,373 B2 | 7/2014 | Bishop et al. |
| 8,906,410 B2 | 12/2014 | Bishop et al. |
| 8,962,239 B2 | 2/2015 | Petkovich et al. |
| 8,992,971 B2 | 3/2015 | Yang |
| 9,017,720 B2 | 4/2015 | Andersen et al. |
| 9,125,823 B2 | 9/2015 | Selva et al. |
| 9,402,855 B2 | 8/2016 | Bishop et al. |
| 9,408,858 B2 | 8/2016 | Bishop et al. |
| 9,498,486 B1 | 11/2016 | Bishop et al. |
| 9,500,661 B2 | 11/2016 | Petkovich et al. |
| 9,861,644 B2 | 1/2018 | White et al. |
| 9,913,852 B2 | 3/2018 | Bishop et al. |
| 9,918,940 B2 | 3/2018 | Bishop et al. |
| 9,943,530 B2 | 4/2018 | Bishop et al. |
| 10,220,047 B2 | 3/2019 | Petkovich et al. |
| 10,300,078 B2 | 5/2019 | White et al. |
| 10,350,224 B2 | 7/2019 | White et al. |
| 10,357,502 B2 | 7/2019 | White et al. |
| 10,493,084 B2 | 12/2019 | Petkovich et al. |
| 2001/0028896 A1 | 10/2001 | Byrd |
| 2001/0036472 A1 | 11/2001 | Wong et al. |
| 2002/0018810 A1 | 2/2002 | Oshlack et al. |
| 2002/0031798 A1 | 3/2002 | Anazawa et al. |
| 2002/0044968 A1 | 4/2002 | van Lengerich |
| 2002/0081331 A1 | 6/2002 | Tanner et al. |
| 2002/0128240 A1 | 9/2002 | Mazess |
| 2002/0155154 A1 | 10/2002 | Wong et al. |
| 2002/0183288 A1 | 12/2002 | Mazess et al. |
| 2003/0059471 A1 | 3/2003 | Compton et al. |
| 2003/0083360 A1 | 5/2003 | Crotts et al. |
| 2003/0129194 A1 | 7/2003 | Mazess et al. |
| 2003/0138482 A1 | 7/2003 | Fonkwe et al. |
| 2003/0152629 A1 | 8/2003 | Shefer et al. |
| 2003/0157560 A1 | 8/2003 | Cantor |
| 2003/0195171 A1 | 10/2003 | Daifotis et al. |
| 2004/0043971 A1 | 3/2004 | Mazess et al. |
| 2004/0092534 A1 | 5/2004 | Yam et al. |
| 2004/0101554 A1 | 5/2004 | Kirschner et al. |
| 2004/0132695 A1 | 7/2004 | Posner et al. |
| 2004/0197407 A1 | 10/2004 | Subramanian et al. |
| 2004/0224930 A1 | 11/2004 | Posner et al. |
| 2004/0258749 A1 | 12/2004 | Guldner et al. |
| 2005/0014211 A1 | 1/2005 | Armbruster et al. |
| 2005/0019374 A1 | 1/2005 | Modliszewski et al. |
| 2005/0037064 A1 | 2/2005 | Basquin et al. |
| 2005/0069579 A1 | 3/2005 | Kamaguchi et al. |
| 2005/0101576 A1 | 5/2005 | Whitehouse et al. |

(56) References Cited

U.S. PATENT DOCUMENTS

| | | |
|---|---|---|
| 2005/0106233 A1 | 5/2005 | Andersen et al. |
| 2005/0124591 A1 | 6/2005 | Tian et al. |
| 2005/0143358 A1 | 6/2005 | DeLuca et al. |
| 2005/0147669 A1 | 7/2005 | Lawrence et al. |
| 2005/0148557 A1 | 7/2005 | Tian et al. |
| 2005/0148558 A1 | 7/2005 | Knutson et al. |
| 2005/0186268 A1 | 8/2005 | Hoshi et al. |
| 2005/0208055 A1 | 9/2005 | Chuang et al. |
| 2005/0287213 A1 | 12/2005 | Wong et al. |
| 2006/0009425 A1 | 1/2006 | Delgado-Herrera et al. |
| 2006/0019933 A1 | 1/2006 | Boardman et al. |
| 2006/0029660 A1 | 2/2006 | Fonkwe et al. |
| 2006/0034937 A1 | 2/2006 | Patel |
| 2006/0057201 A1 | 3/2006 | Bonney et al. |
| 2006/0193877 A1 | 8/2006 | Tengler et al. |
| 2006/0210610 A1 | 9/2006 | Davidson et al. |
| 2006/0223119 A1 | 10/2006 | Cantor |
| 2006/0228808 A1 | 10/2006 | Clarke et al. |
| 2006/0257481 A1 | 11/2006 | Gurney et al. |
| 2007/0026067 A1 | 2/2007 | Yam et al. |
| 2007/0027120 A1 | 2/2007 | Whitehouse et al. |
| 2007/0032461 A1 | 2/2007 | Adorini et al. |
| 2007/0122477 A1 | 5/2007 | Bishop et al. |
| 2007/0155664 A1 | 7/2007 | Ranklove et al. |
| 2007/0190146 A1 | 8/2007 | Roger et al. |
| 2007/0207488 A1 | 9/2007 | Trump et al. |
| 2008/0109983 A1 | 5/2008 | Davis |
| 2008/0134937 A1 | 6/2008 | Yang |
| 2008/0199534 A1 | 8/2008 | Goldberg et al. |
| 2008/0317764 A1 | 12/2008 | Huber et al. |
| 2009/0004284 A1 | 1/2009 | Cheng et al. |
| 2009/0069389 A1 | 3/2009 | Choi et al. |
| 2009/0137536 A1 | 5/2009 | Mazess et al. |
| 2009/0155355 A1 | 6/2009 | Heuer et al. |
| 2009/0176748 A1 | 7/2009 | Tabash et al. |
| 2009/0209501 A1 | 8/2009 | Bishop et al. |
| 2009/0262685 A1 | 10/2009 | Schuringa et al. |
| 2009/0311316 A1 | 12/2009 | Bishop et al. |
| 2010/0120728 A1 | 5/2010 | Petkovich et al. |
| 2010/0144679 A1 | 6/2010 | Lyles |
| 2010/0144684 A1 | 6/2010 | Bishop |
| 2010/0204189 A1 | 8/2010 | Petkovich et al. |
| 2010/0227889 A1 | 9/2010 | Gerspacher et al. |
| 2010/0291191 A1 | 11/2010 | Shoichet et al. |
| 2010/0291197 A1 | 11/2010 | Schwab |
| 2011/0039809 A1 | 2/2011 | Buck et al. |
| 2011/0039810 A1 | 2/2011 | Buck et al. |
| 2011/0039811 A1 | 2/2011 | Buck et al. |
| 2011/0105444 A1 | 5/2011 | Deluca et al. |
| 2011/0118218 A1 | 5/2011 | Buck et al. |
| 2011/0130370 A1 | 6/2011 | Briault et al. |
| 2011/0171298 A1 | 7/2011 | Cao |
| 2011/0182986 A1 | 7/2011 | Speirs et al. |
| 2011/0256230 A1 | 10/2011 | Haeusler et al. |
| 2011/0300210 A1 | 12/2011 | Swanson et al. |
| 2011/0318321 A1 | 12/2011 | Selva et al. |
| 2011/0319503 A1 | 12/2011 | Muller et al. |
| 2012/0015916 A1 | 1/2012 | Tabash et al. |
| 2012/0135103 A1 | 5/2012 | Walsh et al. |
| 2013/0085121 A1 | 4/2013 | Wang et al. |
| 2013/0137663 A1 | 5/2013 | Messner et al. |
| 2013/0178451 A1 | 7/2013 | Bishop et al. |
| 2013/0189522 A1 | 7/2013 | Fujii et al. |
| 2013/0216618 A1 | 8/2013 | Muller et al. |
| 2013/0302309 A1 | 11/2013 | Yang |
| 2014/0088202 A1 | 3/2014 | Cade et al. |
| 2014/0248400 A1 | 9/2014 | Phonchareon et al. |
| 2014/0274977 A1 | 9/2014 | Bishop et al. |
| 2014/0349979 A1 | 11/2014 | White et al. |
| 2014/0357603 A1 | 12/2014 | Bishop et al. |
| 2015/0079165 A1 | 3/2015 | Bishop et al. |
| 2015/0119472 A1 | 4/2015 | Shuai et al. |
| 2015/0119473 A1 | 4/2015 | Shuai et al. |
| 2017/0119677 A1 | 5/2017 | Bishop et al. |
| 2018/0021354 A1 | 1/2018 | Petkovich et al. |

FOREIGN PATENT DOCUMENTS

| | | |
|---|---|---|
| DE | 20321698 U1 | 12/2008 |
| EP | 0 227 836 A1 | 7/1987 |
| EP | 0413828 A1 | 2/1991 |
| EP | 0 508 756 A1 | 10/1992 |
| EP | 0 387 808 B1 | 5/1993 |
| EP | 0629405 A1 | 12/1994 |
| EP | 1080055 A2 | 3/2001 |
| EP | 1208843 A1 | 5/2002 |
| EP | 1 165 061 B1 | 10/2005 |
| EP | 1980255 A1 | 10/2008 |
| EP | 2 148 661 B1 | 12/2012 |
| EP | 2591354 A1 | 5/2013 |
| EP | 2037936 B1 | 6/2014 |
| JP | 55-139320 | 10/1980 |
| JP | 57-188520 | 11/1982 |
| JP | 58-032823 | 2/1983 |
| JP | 58206524 A | 12/1983 |
| JP | 64-031722 | 2/1989 |
| JP | 02-229115 | 9/1990 |
| JP | 04-198129 | 7/1992 |
| JP | 04-208225 A | 7/1992 |
| JP | H04288016 A | 10/1992 |
| JP | 07-242550 A | 9/1995 |
| JP | 08-092098 A | 4/1996 |
| JP | 10-158171 A | 6/1998 |
| JP | 11-158074 | 6/1999 |
| JP | 2001-512418 A | 8/2001 |
| JP | 2002-302447 A | 10/2002 |
| JP | 2004-175750 | 6/2004 |
| JP | 2004-531548 A | 10/2004 |
| JP | 2005-505589 A | 2/2005 |
| JP | 2005-513419 A | 5/2005 |
| JP | 2005-528383 A | 9/2005 |
| JP | 2005-531532 A | 10/2005 |
| JP | 2005-535682 A | 11/2005 |
| JP | 2005-538189 A | 12/2005 |
| JP | 2006-517593 A | 7/2006 |
| JP | 2006-523221 A | 10/2006 |
| JP | 2007-525472 A | 9/2007 |
| JP | 2010-506520 A | 2/2010 |
| JP | 2010-525079 A | 7/2010 |
| JP | 2011-512343 A | 4/2011 |
| JP | 2012-515738 A | 7/2012 |
| KR | 10-2012-0005228 A | 1/2012 |
| WO | WO-91/012807 A1 | 9/1991 |
| WO | WO-91/016899 A1 | 11/1991 |
| WO | WO-92/09271 A1 | 6/1992 |
| WO | WO-94/000128 A1 | 1/1994 |
| WO | WO-96/000074 A1 | 1/1996 |
| WO | WO-96/001621 A1 | 1/1996 |
| WO | WO-96/031215 A1 | 10/1996 |
| WO | WO-97/011053 A1 | 3/1997 |
| WO | WO-98/018610 A1 | 5/1998 |
| WO | WO-98/029105 A2 | 7/1998 |
| WO | WO-99/011272 A1 | 3/1999 |
| WO | WO-99/49027 A1 | 9/1999 |
| WO | WO-99/61398 A2 | 12/1999 |
| WO | WO-00/021504 A1 | 4/2000 |
| WO | WO-00/035419 A2 | 6/2000 |
| WO | WO-00/60109 A1 | 10/2000 |
| WO | WO-00/061123 A2 | 10/2000 |
| WO | WO-01/037808 A1 | 5/2001 |
| WO | WO-01/72286 A1 | 10/2001 |
| WO | WO-0212182 A1 * | 2/2002 ........... C07C 401/00 |
| WO | WO-02/92056 A1 | 11/2002 |
| WO | WO-03/09572 A1 | 1/2003 |
| WO | WO-03/30869 A1 | 4/2003 |
| WO | WO-03/039521 A1 | 5/2003 |
| WO | WO-03/039572 A1 | 5/2003 |
| WO | WO-03/045381 A1 | 6/2003 |
| WO | WO-03/047595 A1 | 6/2003 |
| WO | WO-03/86267 A2 | 10/2003 |
| WO | WO-03/086415 A1 | 10/2003 |
| WO | WO-03/088976 A1 | 10/2003 |
| WO | WO-03/093459 A1 | 11/2003 |
| WO | WO-03/106411 A1 | 12/2003 |
| WO | WO-2004/010981 A1 | 2/2004 |

(56) References Cited

FOREIGN PATENT DOCUMENTS

| | | |
|---|---|---|
| WO | WO-2004/028515 A1 | 4/2004 |
| WO | WO-2004/054968 A2 | 7/2004 |
| WO | WO-2004/058235 A2 | 7/2004 |
| WO | WO-2004/071497 A1 | 8/2004 |
| WO | WO-2004/080467 A2 | 9/2004 |
| WO | WO-2004/098617 A2 | 11/2004 |
| WO | WO-2004/101554 A1 | 11/2004 |
| WO | WO-2004/110381 A2 | 12/2004 |
| WO | WO-2004/110391 A2 | 12/2004 |
| WO | WO-2005/000268 A2 | 1/2005 |
| WO | WO-2005/003358 A1 | 1/2005 |
| WO | WO-2005/011652 A2 | 2/2005 |
| WO | WO-2005/123120 A1 | 12/2005 |
| WO | WO-2006/052452 A1 | 5/2006 |
| WO | WO-2006/059180 A2 | 6/2006 |
| WO | WO-2006/113505 A2 | 10/2006 |
| WO | WO-2007/039193 A1 | 4/2007 |
| WO | WO-2007/039569 A2 | 4/2007 |
| WO | WO-2007/047327 A2 | 4/2007 |
| WO | WO-2007/050724 A2 | 5/2007 |
| WO | WO-2007/050975 A2 | 5/2007 |
| WO | WO-2007/053608 A2 | 5/2007 |
| WO | WO-2007/068287 A1 | 6/2007 |
| WO | WO-2007/092221 A2 | 8/2007 |
| WO | WO-2007/092755 A2 | 8/2007 |
| WO | WO-2007/146004 A1 | 12/2007 |
| WO | WO-2008/008608 A2 | 1/2008 |
| WO | WO-2008/043449 A1 | 4/2008 |
| WO | WO-2008/097646 A1 | 8/2008 |
| WO | WO-2008/116113 | 9/2008 |
| WO | WO-2008/116133 A1 | 9/2008 |
| WO | WO-2008/134512 A1 | 11/2008 |
| WO | WO-2008/134518 A2 | 11/2008 |
| WO | WO-2008/134523 A1 | 11/2008 |
| WO | WO-2009/047644 A2 | 4/2009 |
| WO | WO-2009/101132 A1 | 8/2009 |
| WO | WO-2009/101135 A1 | 8/2009 |
| WO | WO-2009/101137 A1 | 8/2009 |
| WO | WO-2009/124210 A1 | 10/2009 |
| WO | WO-2010/011906 A1 | 1/2010 |
| WO | WO-2010/034342 A1 | 4/2010 |
| WO | WO-2011/031621 A2 | 3/2011 |
| WO | WO-2011/063952 A1 | 6/2011 |
| WO | WO-2011/095388 A1 | 8/2011 |
| WO | WO-2011/123476 A1 | 10/2011 |
| WO | WO-2012/006475 A1 | 1/2012 |
| WO | WO-2012/018329 A1 | 2/2012 |
| WO | WO-2012/076429 A1 | 6/2012 |
| WO | WO-2012/091569 A1 | 7/2012 |
| WO | WO-2012/117236 A1 | 9/2012 |
| WO | WO-2012/145491 A2 | 10/2012 |
| WO | WO-2014/029953 A1 | 2/2014 |
| WO | WO-2014/143941 A1 | 9/2014 |
| WO | WO-2014/193255 A1 | 12/2014 |
| WO | WO-2014/202754 A1 | 12/2014 |
| WO | WO-2016/020508 A2 | 2/2016 |

OTHER PUBLICATIONS

Arekat et al., Dramatic Improvement of BMD Following Vitamin D Therapy in a Bone Marrow Transplant Recipient, J. Clin. Densitometry, 5:267-271 (2002).

Armas et al., Vitamin $D_2$ is Much Less Effective than Vitamin $D_3$ in Humans, J. Clin. Endocrinol. Metab., 89:5387-5391 (2004).

Ashford, Chapter 20: Bioavailability—physicochemical and dosage form factors, pp. 314-333 IN: Aulton et al. (eds.), Aulton's Pharmaceutics. The Design and Manufacture of Medicines, Fourth Edition, Elsevier Publishing (2013).

Bagnis et al., Biochemical and Hormonal Short-Term Effects of 25-hydroxyvitamin D3 in Patients on Continuous Peritoneal Dialysis, Ital. J. Mineral Electrolyte Metab., 12:73-76 (1998).

Bailie et al. Comparative Review of the Pharmacokinetics of Vitamin D Analogues, Seminars in Dialysis, 15(5):352-357 (2000).

Baird et al., Steroid Dynamics Under Steady-State Conditions, Recent Prog. Horm. Res., 25:611-664 (1969).

Barger-Lux M.J. et al., Vitamin D And Its Major Metabolites: Serum Levels After Graded Oral Dosing In Healthy Men Osteoporosis International, United Kingdom, 8(3):222-230 (1998).

Barreto et al., 25-Hydroxyvitamin $D_3$, the Prohormone of 1,25-Dihydroxyvitamin $D_3$, Inhibits the Proliferation of Primary Prostatic Epithelial Cells, Cancer Epidemiol, Biomarkers & Prevention, 9:265-270 (2000).

Beckman, et al., Up-Regulation of the Intestinal 1, 25-Dihydroxyvitamin D Receptor During Hypervitaminosis D: A Comparison Between Vitamin D2 and Vitamin D3 1, Biochemical and Biophysical Research Communications, vol. 169, No. 3, pp. 910-915 (Jun. 29, 1990).

Beer et al., Pharmacokinetics and Tolerability of a Single Dose of DN-101, a New Formulation of Calcitriol, in Patients with Cancer, Clin. Cancer Res., 11:7794-7799 (2005).

Bell et al., Evidence that 1,25-Dihydroxyvitamin D3 Inhibits the Hepatic Production of 25-Hydroxyvitamin D in Man, J. Clin. Invest., 74:1540-1544 (1984).

Belostotsky et al., A single high dose of ergocalciferol can be used to boost 25-hydroxyvitamin D levels in children with kidney disease, Pediatr Nephrol, 24:625-626 (2009).

Bianchi et al., No Difference in Intestinal Strontium Absorption After an Oral or an Intravenous 1,25(OH)2D3 Bolus in Normal Subjects, J. Bone Miner. Res., 14:1789-1795 (1999).

Binkley et al., Laboratory Reporting of 25-Hydroxyvitamin D Results: Potential for Clinical Misinterpretation, Clinical Chemistry, 52(11);2124-2125 (2006).

Blair et al., Prevalence of vitamin D [25(OH)D] deficiency and effects of supplementation with ergocalciferol (vitamin D2) in stage 5 chronic kidney disease patients. J. Ren Nutr., 18:375-382 (2008).

Blunt et al., Biological activity of 25-hydroxycholecalciferol, a metabolite of vitamin D3, Proc. Natl. Acad. Sci. USA, 61(4):1503-6 (1968).

Bordier et al., Evolution of renal osteodystrophy: Correlation of bone histomorphometry and serum mineral and immunoreactive parathyroid hormone values before and after treatment with calcium carbonate or 25-hydroxycholecalciferol, Kidney Int Suppl, 2:S102-S112 (1975).

Boudville et al., Renal Function and 25-Hydroxyvitamin D Concentrations Predict Parathyroid Hormone Levels in Renal Transplant Patients, Nephrol Dial Transplant, 21:2621-2624 (2006).

Bouillon et al., Influence of dialysate calcium concentration and vitamin D on serum parathyroid hormone during repetitive dialysis, Kidney Int., 7:422-432 (1975).

Brossard et al. Influence of Glomerular Filtration Rate on Non-(1-84) Parathyroid Hormone (PTH) Detected by Intact PTH Assays, Clinical Chemistry, 46(5):697-703 (2000).

Brown et al., The Vitamin D Prodrugs 1α(OH)$D_2$, 1α(OH)$D_3$ and BCI-210 Suppress PTH Secretion by Bovine Parathyroid Cells, Nephrol Dial Transplant, 21:644-650 (2006).

Brown et al., Vitamin D Analogues for Secondary Hyperparathyroidism, Nephrol Dial Transplant, 17[Suppl. 10]:10-19 (2002).

Buccianti et al., Effects of Calcifediol Treatment on the Progression of Renal Osteodystrophy during Continuous Ambulatory Peritoneal Dialysis, Nephron, 56:353-356 (1990).

Budavari (ed.), Merck Index: an Encyclopedia of Chemicals, Drugs, and Biologicals, 11th Edition, Merck & Co., 9927-9930 (1989).

Bulla et al., Renal bone disorders in children: therapy with vitamin D3 or 1,25-dihydroxycholecalciferol, Proc.Eur.Dial.Transplant. Assoc., 16: 644-648 (1979).

Chandra et al., Cholecalciferol (vitamin D3) therapy and vitamin D insufficiency in patients with chronic kidney disease: a randomized controlled pilot study, Endocr.Pract., 14: 10-17 (2008).

Claris-Appiani et al., Phosphate-Induced PTH Stimulation and Calcitriol Treatment in Children with Early Chronic Renal Insufficiency, J. Bone Miner. Met., 12:S91-S97 (1994).

Coburn et al., Doxercalciferol Safely Suppresses PTH Levels in Patients with Secondary Hyperparathyroidism Associated with Chronic Kidney Disease Stages 3 and 4, Am. J. Kidney Dis., 43(5):877-890 (2004).

(56) References Cited

OTHER PUBLICATIONS

Coburn, An Update on Vitamin D as Related to Nephrology Practice: 2003, Kidney International, vol. 64, Supplement 87, pp. S125-S130 (2003).
Coburn, et al., Use of Active Vitamin D Sterols in Patients with Chronic Kidney Disease, Stages 3 and 5, Kidney International, vol. 63, Supplement 85, pp. S49-S53 (2003).
Coen et al., 1,25(OH)2D3 and 25-OHD3 in the Treatment of Renal Osteodystrophy: Comparison of Combined Versus 1,25(OH)2D3 Administration Alone, Miner. Electrolyte Metab., 9:19-27 (1983).
Coen et al., 25-hydroxycholecalciferol in the treatment of renal osteodystrophy in haemodialysed patients, Int J Artificial Organs, 2(6): 278-281 (1979).
Cohen-Solal et al., Non-Aluminic Adynamic Bone Disease in Non-Dialyzed Uremic Patients: A New Type of Osteopathy Due to Overtreatment? Bone, 13:1-5 (1992).
Collet et al. Modified-Release Peroral Dosage Forms, Aulton (ed.), Pharmaceutics: The Science of Dosage Forms, Churchill Livingston, London, pp. 289-305 (2002).
Colodro et al., Effect of 25-Hydroxy-Vitamin D3 on Intestinal Absorption of Calcium in Normal Man and Patients With Renal Failure, Metabolism, 27(6):745-753 (1978).
Cooke et al., Vitamin D-Binding Protein (Gc-Globulin): Update 1995, Endocrine Rev., 4:125-128 (1995).
Coyne et al., Paricalcitol Capsule for the Treatment of Secondary Hyperparathyroidism in Stages 3 and 4 CKD, American Journal of Kidney Diseases, 47(2):263-276 (2006).
Daisley-Kydd et al., Calcitriol in the Management of Secondary Hyperparathyroidism of Renal Failure, Pharmacotherapy., 16:619-630 (1996).
Davies, M. et al. The Absorption and Metabolism of Vitamin D3 from Parenteral Injection Sites, Proceedings of the Workshop on Vitamin D, 4th, Vitam. D: Basic Res. Its Clin. Appl. (1979), abstract.
DB-Pharma, Dedrogyl 15 Mg/10ML Calcifediol Oral Drops, Solution, Marketing Authorization No. 317 863.2 (2000).
DeLuca, Treatment of renal osteodystrophy with 25-hydroxycholecalciferol, Arch Intern Med, 126(5):896-899 (1970).
Deroisy et al., Comparison of the Short-Term Effects of Three Oral Calcium-Vitamin D Formulations and Placebo on Calcium Metabolism, Curr. Ther. Res., 59:370-378 (1998).
DeVille et al., Effect of Ergocalciferol Supplementation on Serum Parathyroid Hormone and Serum 25-Hydroxyvitamin D in Chronic Kidney Disease, Nephrology, 11:555-559 (2006).
Dietary Reference Intakes for Calcium, Phosphorus, Magnesium, Vitamin D, and Fluoride, Standing Committee on the Scientific Evaluation of Dietary Reference Intakes, Food and Nutrition Board, Institute of Medicine, National Academy Press, Washington DC, pp. 250-287 (1997).
Dietary Supplement Fact Sheet: Vitamin D, National Institutes of Health, Office of Dietary Supplements (last update: Aug. 5, 2005), retrieved from <URL: http:ods.od.nih.gov/factsheets/vitamind.asp> on Aug. 31, 2007.
Disease and Vitamin D, University of California Riverside, retrieved from Internet, <URL: <http://vitamind.ucr.edu/disease.html>> (last update: May 19, 1999).
Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.
Dogan et al., Effect of depot oral cholecalciferol treatment on secondary hyperparathyroidism in stage 3 and stage 4 chronic kidney diseases patients, Ren Fail., 30: 407-410 (2008).
Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).
Dusso et al, Metabolic Clearance Rate and Production Rate of Calcitriol in Uremia, Kidney Int., 35 860-864 (1989).

Dusso et al., Extra-renal production of calcitriol in chronic renal failure, Kidney Int., 34:368-375 (1988).
Dusso et al., Extrarenal Production of Calcitrol in Normal and Uremic Humans*, Journal of Clinical Endocrinology and Metabolism, 72(1):157-164 (1991).
Eastwood et al., Biochemical and histological effects of 1,25 dihydroxycholecalciferol (1,25-DHCC) in the osteomalacia of chronic renal failure, J Urol Nephrol (Paris,) 80(12): 984-985 (1974).
Eastwood et al., The contrasting effects on bone histology of vitamin D and of calcium carbonate in the osteomalacia of chronic renal failure, Clin Sci Molec Med, 47:23-42 (1974).
Eastwood et al., The Effect of 25-Hydroxy Vitamin D3 in the Osteomalacia of Chronic Renal Failure, Clin. Sci. Molec. Med., 52:499-508 (1977).
Fernandez et al., Guidelines for Dosing of Intravenous Calcitriol in Dialysis Patients with Hyperparathyroidism, Nephrol. Dial. Transplant., 11:96-101 (1996).
Fournier et al., 1-alpha-Hydroxycholecalciferol and 25-Hydroxycholecalciferol in Renal Bone Disease, Calcified Tissues 1975: Proceedings of the 11th European Symposium on Calcified Tissues, 226-235 (1975).
Fournier et al., 1α Hydroxycholecalciferol and 25 Hydroxycholecalciferol in Renal Bone Disease Proc Eur Dial Transplant Assoc 12:227-236 (1976).
Fournier et al., 1α-hydroxycholecalciferol and 25-hydroxycholecalciferol in Renal Bone Disease Calcif Tissue Res. 21:226-235 (1976).
Fournier et al., Advances in Nephrology from the Necker Hospital Adv. Nephrol Necker Hosp. 21:237-306 (1992).
Fournier et al., Comparison of 1α-hydroxycholecalciferol and 25-hydroxycholecalciferol in the treatment of renal osteodystrophy: Greater effect of 25-hydroxycholecalciferol on bone mineralization Kidney International 15:196-204 (1979).
Fournier et al., Current Status of the Management of Renal Osteodystrophy Proceedings of the European Dialysis and Transplant Association 15:547-568 (1978).
Fournier et al., Importance of Vitamin D Repletion in Uraemia, Nephrol Dial Transplant, 14(4):819-823 (1999).
Fournier et al., Low doses of calcitriol or calcium carbonate for the prevention of hyperparathyroidism in predialysis patients? Nephrol Dial Transplant 11(7):1493-1495 (1996).
Fournier et al., Present-Day Concepts in the Treatment of Chronic Renal Failure Contrib Nephrol. 71:64-80 (1989).
Fournier et al., Preventing Renal Bone Disease in Moderate Renal Failure with CaCO3 and 25(OH) Vitamin D3, Kidney Int., 33:S178-S279 (1988).
Fournier et al., Renal Osteodystrophy in Dialysis Patients: Diagnosis and Treatment, Artificial Organs, 22:530-557 (1998).
Fournier et al., Renal Osteodystrophy: Pathophysiology and Treatment Hormone Res. 20:44-58 (1984).
Fournier et al., The Approach to the Treatment of Secondary Hyperparathyroidism in Early Renal Failure Am. J. Nephrol 8:170-172 (1988).
Fournier et al., Traitement vitaminique D et ostéodystrophies rénales: indications et modalitiés Nephrologie 16(2):165-190 (1995) [journal in French].
Fournier, Vitamin D: Biochemical, Chemical, and Clinical Aspects Related to Calcium Metabolism, Vitamin D: Proceedings of the Third Workshop on Vitamin D, Asilomar, Pacific Grove, CA, USA 667-669 (1977).
Friedman et al. The Role of Vitamin D in Mild to Moderate Chronic Kidney Disease, Trends in Endocrinology & Metab,. 13(5):189-194 (2002).
Fritsche et al., Regulation of 25-Hydroxyvitamin $D_3$-1α-Hydroxylase and Production of 1α,25-Dihydroxyvitamin $D_3$ by Human Dendritic Cells, Blood, 102(9):3314-3316 (2003).
Frohling et al., Serum 25-hydroxyvitamin D in patients with chronic renal failure on long-term treatment with high doses of vitamin D2. Nephron 26: 116-120 (1980).
Frost et al., Histomorphometric Changes in Trabecular Bone of Renal Failure Patients Treated with Calcifediol, Metab. Bone Dis. & Rel. Res., 2:285-295 (1981).
Gallagher et al., Comparison of the Histological Effect and Metabolism of 25-(OH)D and 1,25-(OH)2D in Rat Bone, p. 399-401, IN:

(56) References Cited

OTHER PUBLICATIONS

Norman, Vitamin D: Basic Research and its Clinical Application: Proceedings of the Fourth Workshop on Vitamin D, Berlin, West Germany, Feb. 1979.
Ghazali et al., Is low plasma 25-(OH) vitamin D a major risk factor for hyperparathyroidism and Looser's zones independent of calcitriol? Kidney International 55:2169-2177 (1999).
Gibson, ed., Product optimisation. Pharmaceutical Preformulation and Formulation: A Practical Guide from Candidate Drug Selection to Commercial Dosage Form, 295-8 (2004).
Granja et al., Studies on the Opening of Dioxanone and Acetal Templates and Application to the Synthesis of 1α,25-Dihydroxyvitamin $D_2^1$, J. Org. Chem., 58:124-131 (1993).
Gómez-Alonso et al., Vitamin D Status and Secondary Hyperparathyroidism: The Importance of 25-Hydroxyvitamin D Cut-Off Levels, Kidney International, 63(Supp. 85):S44-S48 (2003).
Haddad et al., Acute Administration of 25-Hydroxycholecalciferol in Man, J. Clin. Endocrinol. Metab., 42:284-289 (1976).
Haddad et al., Human Serum Binding Capacity and Affinity for 25-Hydroxyergocalciferol and 25-Hydroxycholecalciferol, J. Clin. Endocrinol. Metab., 43:86-91 (1976).
Haddad et al., Natural and Synthetic Sources of Circulating 25-Hydroxyvitamin D in Man, Nature, 244:515-517 (1973).
Haddad et al., Vitamin D plasma binding protein. Turnover and fate in the rabbit, J. Clin. Invest., 67(5):1550-60 (1981).
Haddad, Plasma Vitamin D-binding Protein (Gc-Globulin): Multiple Tasks, J. Steroid Biochem. Molec. Biol., 53:579-582 (1995).
Haddad, Seasonal Diminution of Vitamin D Stores in the United States: Can Darker Winters Lead to Lighter Bones? Trends Endocrinol. Metab., 7:209-212 (1996).
Haddad, Traffic, Binding and Cellular Access of Vitamin D Sterols, Bone and Mineral Res., Elsevier, 5:281-308 (1987).
Haddad, Vitamin D—Solar Rays, The Milky Way, or Both? NEJM, 326:1213-1215 (1992).
Haldimann et al., Effect of an Oral Dose of 25-Hydroxyvitamin D3 on Its Blood Levels in Patients with the Nephrotic Syndrome, J Clin Endocrinology and Metabolism, 50(3): 470-474 (1980).
Halloran et al., Plasma Vitamin D Metabolite Concentrations in Chronic Renal Failure: Effect of Oral Administration of 25-Hydroxyvitamin D3, J. Clin. Endocrin. & Metab., 59:1063-1069 (1984).
Hamida et al., Hyperparathyroïdie secondaire álinsuffisance rénale Annales d'Endocrin-ologie 55:147-158 (1994) [reference in French].
Hannula et al., Constant, But Not Pulsed Calcitriol Suppresses Hemodialysis Patients' Antigen-Induced Lymphocyte Proliferation, Nephron, 86:139-144 (2000).
Hari et al., Vitamin D insufficiency and effect of cholecalciferol in children with chronic kidney disease, Pediatr.Nephrol,. 25: 2483-2488 (2010).
Hay et al., Vitamin D2 in Vertebrate Evolution, Comp. Biochem. Physiol. B, 56:375-380 (1977).
Hectorol® (doxercalciferol) Capsules (Label, FDA, 2010).
Hodson et al., Treatment of childhood renal osteodystrophy with calcitriol or ergocalciferol, Clin Nephrology, 24(4): 192-200 (1985).
Holick, Vitamin D Deficiency in CKD: Why Should We Care? Am. J. Kidney Dis., 45:1119-1121 (2005).
Holick, Vitamin D Status: Measurement, Interpretation and Clinical Application, Ann Epidemiol, 19(2):73-78 (2009).
Hollis, Circulating 25-Hydroxyvitamin D Levels Indicative of Vitamin D Sufficiency: Implications for Establishing a New Effective Dietary Intake Recommendation for Vitamin D, J. Nutr. 135: 317-322 (2005).
Holmberg et al., Absorption of a pharmacological dose of vitamin D3 from two different lipid vehicles in man: comparison of peanut oil and a medium chain triglyceride, Biopharm. Drug Dispos., 11(9):807-15 (1990).
Horst et al., A Sensitive Competitive Protein Binding Assay for Vitamin D in Plasma, Steroids, 37:581-592 (1981).
Horst et al., Discrimination in the Metabolism of Orally Dosed Ergocalciferol and Cholecalciferol by the Pig, Rat and Chick, Biochem. J., 204:185-189 (1982).
Horst et al., Rat cytochrome P450C24 (CYP24) does not metabolize 1,25-dihydroxyvitamin D2 to calcitroic acid, J. Cell Biochem., 88:282-285 (2003).
Hottelart et al., Ostéodystrophie rénale (2): son traitement chez l'insuffisant rénal avant la dialyse Nephrologie 21(6):275-282 (2000) [reference in French].
Houghton et al., The Case Against Ergocalciferol (Vitamin D2) as a Vitamin Supplement, Am. J. Clin. Nutr., 84:694-697 (2006).
Hunt, et al., A Comparison of the Toxicity of Ergocalciferol and Cholecalciferol in Rhesus Monkeys (*Macaca mulatta*), J. Nutrition, 102:975-986 (1972).
Hussar, New Drugs of 1999, J. Am. Pharmacist. Assoc. 40(2):181-229 (2000).
Iladdad, Plasma Vitamin D-binding Protein (Gc-Globulin): Multiple Tasks, J. Steriod Biochem. Molec. Biol., 53:579-582 (1995).
International Search Report for Application No. PCT/US2007/061521, dated Jul. 17, 2007.
International Search Report of counterpart PCT/US2008/061579 dated Aug. 21, 2008 (5 pages).
International Search Report of PCT/US2008/061579 dated Aug. 21, 2008 (5 pages).
Ishimura et al., Serum Levels of 1,25-Dihydroxyvitamin D, 24,25-Dihydroxyvitamin D, and 25-Hydroxyvitamin D in Nondialyzed Patients with Chronic Renal Failure, Kidney Int., 55:1019-1027 (1999).
Japanese Office Action for Application No. 2008-553520, dated Jul. 24, 2013.
Jara et al., Effect of Calcitriol Treatment and Withdrawal on Hyperparathyroidism in Haemodialysis Patients with Hypocalcaemia, Nephrol. Dial. Transplant., 16:1009-1016 (2001).
Jean et al., Daily Oral 25-Hydroxycholecalciferol Supplementation for Vitamin D Deficiency in Haemodialysis Patients: Effects on Mineral Metabolism and Bone Markers, Nephrol. Dial. Transplant, 23:3670-3676 (2008).
Jean et al., Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment Nephron. Clin. Pract. 110:c58-c65 (2008).
Jean et al., Monthly cholecalciferol administration in heamodialysis patients: a simple and efficient strategy for vitamin D supplementation Nephrol. Dial. Transplant 24(12):3799-3805 (2009).
Jones, Pharmacokinetics of vitamin D toxicity, Am. J. Clin. Nutr. 88(suppl): 582S-6S (2008).
Jones., Expanding the Role for Vitamin D in Chronic Kidney Disease: Importance of Blood 25-OH-D Levels and Extra-Renal 1α-Hydroxyase in the Classical and Nonclassical Actions of 1α, 25-Dihydroxyvitamin D3, Seminars in Dialysis, 20(4):316-324 (2007).
Kajihara et al., Novel Method to Control Release of Lipophilic Drugs with High Potency from Silicone, Chem. Pharm. Bull., 51:11-14 (2003).
Kalantar-Zadeh et al., Clinical Outcomes with Active versus Nutritional Vitamin D Compounds in Chronic Kidney Disease Clin J Am Soc Nephrol. 4(9):1529-1539 (2009).
Kanis et al., Rate of Reversal of Hypercalcaemia and Hypercalciuria Induced by Vitamin D and Its 1-alpha-Hydroxylated Derivatives, BMJ, 1:78-81 (1977).
Khachane et al., Novel Suatained Release Drug Delivery System: Review, IJPRD, 3(12):1-14 (2012).
Kidney Disease Improving Global Outcomes (KDIGO) 2017 Clinical Practice Guideline Update for the Diagnosis, Evaluation, Prevention, and Treatment of Chronic Kidney Disease-Mineral and Bone Disorder (CKD-MBD). Kidney Int Suppl. 2017;7(1):1-59.
Kim, Advanced Pharmaceutics: Physicochemical Principles, pp. 362-392, Boca Raton, Fla: CRC Press (2004).
Kinoshita et al., 1,25-Dihydroxyvitamin D Suppresses Circulating Levels of Parathyroid Hormone in a Patient with Primary Hyperparathyroidism and Coexistent Sarcoidosis, J. Clin. Endo. & Metabol., 90(12):6727-6731 (2005).
Kleinman et al., Effects of Calcifediol on Calcified Tissue in Uremia, Arch Intern Med, 138: 864-865 (1978).

(56) References Cited

OTHER PUBLICATIONS

Kobayashi et al., 2β-(3-Hydroxyproxy)-α,25-Dihydroxyvitamin $D_3$ (ED-71), Preventive and Therapeutic Effects on Bone Mineral Loss in Ovariectomized Rats, Bioorganic & Medicinal Chemistry Letters, 3(9):1815-1819 (1993).
Kobayashi et al., Variation of 25-Hydroxyvitamin D3 and 25-Hydroxyvitamin D2 Levels in Human Plasma Obtained from 758 Japanese Healthy Subjects, J. Nutr. Sci. Vitaminol (Tokyo), 29(3):271-281 (1983). Abstract Only.
Kooienga et al., The effect of combined calcium and vitamin D3 supplementation on serum intact parathyroid hormone in moderate CKD, Am.J.Kidney Dis,. 53: 408-416 (2009).
Koshikawa, et al., Clinical Effect of Intravenous Calcitriol Administration on Secondary Hyperparathyroidism, Nephron; 90:413-423 (2002).
Kovesdy et al., Association of activated vitamin D treatment and mortality in chronic kidney disease, Arch. Intern. Med., 168(4):397-403 (Feb. 2008).
LaClair et al., Prevalence of Calcidiol Deficiency in Ckd: A Cross-Sectional Study Across Latitudes in the United States, Am. J. Kidney Dis., 45:1026-1033 (2005).
Lafage et al., Ketodiet, Physiological Calcium Intake and Native Vitamin D Improve Renal Osteodystrophy, Kidney Int., 42:1217-1225 (1992).
Lambert et al., Evidence for Extranrenal Production of 1-alpha,25-Dihydroxyvitamin D in Man, J. Clin. Invest., 69:722-725 (1982).
Lambrey et al., 24, 25 Dihydroxycalciferol: Assay in Non-Anephric Patients on Chronic Haemodialysis and Assessment of it's Possible Pathophysiological Role in Renal Osteodystrophy Proc Eur Dial Transplant Assoc. 17:548-556 (1980).
Lambrey, Possible Link Between Changes in Plasma 24,25-Dihydroxyvitamin D and Healing of Bone Resorption in Dialysis Osteodrstrophy Metab. Bone Dis. & Rel. Res. 4:25-30 (1982).
Langman et al., 25-Hydroxyvitamin D3 (Calcifediol) Therapy of Juvenile Renal Osteodystrophy: Beneficial Effect on Linear Growth Velocity, J. Pediatrics, 100:815-820 (1982).
Larrosa M. et al., Long-Term Treatment of Hypovitaminosis D. Calcidol Or Cholecalciferol? Annals Of The Rheumatic Diseases, vol. 64, No. Suppl. 3, Jul. 2005, p. 366.
Lau et al., Vitamin D Therapy of Osteoporosis: Plain Vitamin D Therapy Versus Active Vitamin D Analog (D-Hormone) Therapy, Calcif. Tissue Int., 65:295-306 (1999).
Lehmann et al., Coating of Tablets and Small Particles with Acrylic Resins by Fluid Bed Technology, Int. J. Pharm. Tech. & Prod. Mfr., 2:31-43 (1981).
Letteri et al., Effects of 25-Hydroxycholecalciferol on Calcium Metabolism in Chronic Renal Failure Adv. Exp. Med. Biol. 81:591-601 (1977).
Lips et al., A Global Study of Vitamin D Status and Parathyroid Function in Postmenopausal Women with Osteoporosis: Baseline Data from the Multiple Outcomes of Raloxifene Evaluation Clinical Trial, The Jour. of Clin. Endo. & Meta., 86(3):1212-1221 (2001).
Lo et al., Vitamin D absorption in healthy subjects and in patients with intestinal malabsorption syndromes, Am. J. Clin. Nutr., 42(4):644-9 (1985).
Lomonte et al., Are Low Plasma Levels of 25-(OH) Vitamin D a Major Risk Factor for Hyperparathyroidism Independent of Calcitriol in Renal Transplant Patients? J. Nephrol., 18:96-101 (2005).
Lund et al., Serum 1,25-Dihydroxycholecalciferol in Anephric. Haemodialyzed and Kidney-transplanted Patients, Nephron, 25:30-33 (1980).
Maierhofer et al., Synthesis and Metabolic Clearance of 1,25-Dihydroxyvitamin D as Determinants of Serum Concentrations: a Comparison of Two Methods Journal of Clinical Endocrinology and Metabolism 53:472-475 (1981).
Manni et al., Oral Calcitriol: Comparison Between the Same Weekly Dose Administered as a Single vs. Two Divided Pulsed Doses in Secondary Hyperparathyroidism of Chronic Renal Failure, Ital. J Mineral Electrolyte Metab., 11:61-64 (1997).

Martin et al., 19-Nor-1-α-25-Dihydroxyvitamin $D_2$ (Paricalcitol) Safely and Effectively Reduces the Levels of Intact Parathyroid Hormone in Patients on Hemodialysis, J. Am. Soc. Nephrol., 9:1427-1432 (1998).
Matsushita et al., Clinical effects of 25-hydroxycholecalciferol in patients with chronic renal failure, J Nutr Sci Vitaminol, 23:257-261 (1977).
Mazouz et al., Risk factors of renal failure progression two years prior to dialysisis Clinical Nephroloby 51(6):355-366 (1999).
Mazur, Effects of 25-OHD3 on Renal Function in Pediatric Patients with Chronic Renal Failure, Mineral Electrolyte Metab. 10:351-358 (1984).
Memmos et al., Response of uremic osteoid to vitamin D, Kidney Int, 21 (Suppl. 11): S50-S54 (1982).
Menon et al., Vitamin D insufficiency and hyperparathyroidism in children with chronic kidney disease, Pedaitr Nephrol, 23:1831-1836 (2008).
Messa et al., Direct In Vivo Assessment of Parathyroid Hormone-Calcium Relationship Curve in Renal Patients, Kidney Int., 46:1713-1720 (1994).
Minutes of US FDA E&M Advisory Committee Meeting of Oct. 4, 1979 for Calderol® calcifediol capsules.
Moe et al., A randomized trial of cholecalciferol versus doxercalciferol for lowering parathyroid hormone in chronic kidney disease, Clin. J.Am.Soc.Nephrol. 5: 299-306 (2010).
Moe et al., Safety and Efficacy of Pulse and Daily Calcitriol in Patients on CAPD: A Randomized Trial, Nephrol. Dial. Transplant., 13:1234-1241 (1998).
Morris, Cats Discriminate Between Cholecalciferol and Ergocalciferol, J. Anim. Physiol. a. Anim. Nutr., 86:229-238 (2002).
Morris, Vitamin D: A Hormone for All Seasons—How Much is Enough? Clin. Biochem. Rev., 26:21-32 (2005).
Muindi et al., Phamacokinetics of Liquid Calcitriol Formulation in Advanced Solid Tumor Patients: Comparison with Caplet Formulation, Cancer Chemother. Pharmacol., 56:492-496 (2005).
Naik et al., Effects of Vitamin D Metabolites and Analogues on Renal Function, Nephron, 28:17-25 (1981).
Nakanishi et al., The Roles of Vitamin D in Secondary Hyperparathyroidism, [journal in Japanese] 52:1107-1112 (2004).
Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Notice of allowance dated Jul. 10, 2012, in counterpart EPO application 08746908.6.
Oksa et al., Effects of long-term cholecalciferol supplementation on mineral metabolism and calciotropic hormones in chronic kidney disease, Kidney Blood Press Res., 31: 322-329 (2008).
Parfitt et al., Calcitriol But No Other Metabolite of Vitamin D is Essential for NormalBone Growth and Development in the Rat, J. Clin. Invest., 73:576-586 (1984).
Patel et al., Glomerular Filtration Rate is a Major Determinant of the Relationship Between 25-Hydroxyvitamin D and Parathyroid Hormone, Calcif. Tissue Int., 80:221-226 (2007).
Peacock et al., Effect of Calcium or 25OH Vitamin D3 Dietary Supplementation on Bone Loss at the Hip in Men and Women over the Age of 60 The Journal of Clinical Endocrinology & Metabolism, 85(9):3011-3019 (2007).
Perrie, Pharmaceutics: Drug Delivery and Targeting, Second Edition, Chapter 1 (2012).
Phadnis et al., Direct, Rapid Effects of 25-Hydroxyvitamin D3 on Isolated Intestinal Cells, J. Cell. Biochem., 90:287-293 (2003).
Pourgholami et al., 1, 25-Dihydroxyvitamin D3 Dissolved in Lipiodol Produces a Sustained Antiproliferative Effect in the Human Hepatoblastoma Cell Line HepG2, Anticancer Res., 20:723-728 (2000).
Pourgholami et al., In Vitro Antiproliferative Activity of a Medium-Chain Triglyceride Solution of 1, 25-Dihydroxyvitamin $D_3$ in HepG2 Cells, Anticancer Res., 20:4257-4260 (2000).
Prescribing Information for Calderol® calcifediol capsules (1988).
Prescribing Information for Hectorol® (doxercalciferol capsules), Genzyme (2011).

(56) References Cited

OTHER PUBLICATIONS

Prescribing information for Zemplar® (paricalcitol) Capsules, Abbott (2011).
Querfeld et al., Vitamin D deficiency and toxicity in chronic kidney disease: in search of the therapeutic window, Pediatr. Nephrol., 25(12):2413-30 (Dec. 2010).
Rambeck et al., Biological Activity of 1α,25-Dihydroxyergocalciferol in Rachitic Chicks and in Rats, IZVIAK, 54(2/3):135-139 (1984).
Rapuri, P.B. et al., Effect of Vitamins D2 and D3 Supplement Use on Serum 25-OHD Concentration in Elderly Women in Summer and Winter, Calcified Tissue International, 74(2):150-156 (2004).
Ravani et al., Vitamin D levels and patient outcome in chronic kidney disease, Kidney Int., 75(1):88-95 (Jan. 2009).
Recker et al., The Efficacy of Calcifediol in Renal Osteodystrophy, Arch. Intern. Med., 138:857-863 (1978).
Reddy et al., Abstracts Sixth Annual Scientific Meeting of the American Society for Bone and Mineral Research, 36:524 (1984).
Reichel et al., Calcium Metabolism in Early Chronic Renal Failure: Implications for the Pathogenesis of Hyperparathyroidism, Nephrol. Dial. Transplant., 6:162-169 (1991).
Reichel et al., Intermittent Versus Continuous Administration of 1,25-dihydroxyvitamin D3 in experimental renal hyperparathyroidism, Kidney Int., 44:1259-1265 (1993).
Reichel, Current treatment options in secondary renal hyperparathyroidism, Nephrol Dial Transplant 21:23-28 (2006).
Ritter et al., 25-Hydroxyvitamin D3 suppresses PTH synthesis and secretion by bovine parathyroid cells, Kidney Int., 70:654-659 (2006).
Rix et al., Effect of 18 Months of Treatment with Alfacalcidol on Bone in Patients with Mild to Moderate Chronic Renal Failure, Nephrol Dial Transplant, 19:870-876 (2004).
Rucker et al., Vitamin D insufficiency and treatment with oral vitamin D3 in northern-dwelling patients with chronic kidney disease, J.Nephrol. 22: 75-82 (2009).
Russell et al., Therapeutic Effects of 25-Hydroxyvitamin D3 on Renal Osteodystrophy, Mineral Electrolyte Metab., 1:129-138 (1978).
Rutherford et al., Effect of 25-Hydroxycholecalciferol on Calcium Absorption in Chronic Renal Disease, Kidney International, 8:320-324 (1975).
Saab et al., Prevalence of Vitamin D Deficiency and the Safety and Effectiveness of Monthly Ergocalciferol in Hemodialysis Patients, Nephron Clin. Pract., 105:c132-c138 (2007).
Sanchez, Prevention and Treatment of Renal Osteodystrophy in Children With Chronic Renal Insufficiency and End-Stage Renal Disease, Seminars in Nephrology, 21:441-450 (2001).
Schmidt, Measurement of 25-Hydroxyvitamin D Revisited, Clinical Chemistry, 52(12):2304-2305 (2006).
Sebert et al. Comparative effects of equal doses of vitamin D2 and vitamin D3 for the correction of vitamin D deficiency in the elderly in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Sebert et al., Effets A Long Terme D'Une Association De 25-Hydroxycholécalciférol et de 1-Alpha-Hydroxycholécalciférol Sur L'Ostéodystrophie Des Hémodialysés Chroniques Rev. Rhum Mal Osteoartic 48(7-9):535-541 (1981).
Sebert et al., Limit by Hyperphosphatemia of the Usefulness of Vitamin D Metabolites (1 alpha-Hydroxycholecalciferol and 25-Hydroxycholecalciferol) in the Treatment of Renal Osteodystrophy, Metab. Bone Dis. & Rel. Res., 2:217-222 (1980).
Sekkarie, The Impact of Over-the-counter Vitamin D Supplementals on Vitamin D and Parathyroid Hormone Levels in Chronic Kidney Disease, Clin. Nephrology, 65:91-96 (2006).
Shah et al., Prevalence and correction of 25(OH) vitamin D deficiency in peritoneal dialysis patients, Peritoneal Dialysis Int., 25:362-366 ( 2005).
Shi et al., Preparation of Chitosan/Ethylcellulose Complex Microcapsule and its Application in Controlled Release of Vitamin $D_2$, Biomaterials, 23:4469-4473 (2002).
Singh et al., C-3 Epimers Can Account for a Significant Proportion of Total Circulating 25-Hydroxyvitamin D in Infants, Complicating Accurate Measurement and interpretation of Vitamin D Status, J. Clin. Endo. & Metabol., 91(8):3055-3061 (2006).
Sitrin et al., Comparison of vitamin D and 25-hydroxyvitamin D absorption in the rat, Am. J. Physiol., 242(4):G326-32 (1982).
Sjoden, et al., 1α-Hydroxyvitamin D2 is Less Toxic than 1α-Hydroxyvitamin D3 in the Rat, Society for Experimental Biology and Medicine, 179: 432-436 (1985).
Skelly et al., In vitro and in vivo testing an correlation for oral controlled/modified-release dosage forms. Pharm. Res., 7(9):975-82 (1990).
Slatopolsky et al., Differential Effects of 19-nor-1,25-$(OH)_2D_2$ and 1α-Hydroxyvitamin $D_2$ on Calcium and Phosphorus in Normal and Uremic Rats, Kidney International, 62:1277-1284 (2002).
Somerville et al., Resistance to Parathyroid Hormone in Renal Failure: Role of Vitamin D Metabolites, Kidney Int., 14:245-254 (1978).
Sommerfeldt et al., Metabolism of Orally Administered [3H]Ergocalciferol and [3H]Cholecalciferol by Dairy Calves, J. Nutr., 113:2595-2600 (1983).
Sosa et al., The Effect of 25-dihydroxyvitamin D on the Bone Mineral Metabolism of Elderly Women with Hip Fracture, Rheumatology, 39:1263-1268 (2000).
Stamp et al., Comparison of Oral 25-Hydroxycholecalciferol, Vitamin D, and Ultraviolet Light as Determinants of Circulating 25-Hydroxyvitamin D, The Lancet, 1341-1343 (Jun. 25, 1977).
Stamp, Intestinal Absorption of 25-hydroxycholecalciferol, The Lancet, 121-123 (1974).
Stavroulopoulos et al., Relationship between vitamin D status, parathyroid hormone levels and bone mineral density in patients with chronic kidney disease stages 3 and 4, Nephrology (Carlton), 13(1):63-7 (Feb. 2008).
Stein et al., An Update on the Therapeutic Potential of Vitamin D Analogues, Expert Opin. Investig. Drugs, 12:825-840 (2003).
Stubbs et al., Cholecalciferol supplementation alters calcitriol-responsive monocyte proteins and decreases inflammatory cytokines in ESRD, J.Am.Soc.Nephrol., 21: 353-361 (2010).
Stumpf, The Dose Makes the Medicine, Drug Discovery Today, 11:550-555 (2006).
Szycher, Szycher's Dictionary of Biomaterials and Medical Devices, pp. 20, 48, 127, Lancaster, Penn: Technomic Publishing Co., Inc. (1992).
Sömjen et al., Nonhypercalcemic Analogs of Vitamin D Stimulate Creatine Kinase B Activity in Osteoblast-Like ROS 17/2.8 Cells and Up-Regulate Their Responsiveness to Estrogens, Steroids, 63:340-343 (1998).
Tamez et al., Vitamin D reduces left atrial volume in patients with left ventricular hypertrophy and chronic kidney disease, Am. Heart J., 164(6):902-9.e2 (Dec. 2012).
Taylor et al., Interrelationship of Serum 25-Hydroxyvitamin D3 and 1,25-Dihydroxyvitamin D in Juvenile Renal Osteodystrophy after Therapy with 25-Hydroxyvitamin D3, Metab. Bone Dis. & Rel. Res., 4:255-261 (1982).
Taylor et al., The absence of 24,25-dihydroxycholecalciferol in anephric patients, Clin.Sci.Mol.Med.Suppl., 55: 541-547 (1978).
Taylor, CM, 24,25-Dihydroxyvitamin D in Human Serum. In: Vitamin D. Basic Research and Clinical Applications, pp. 197-203. Walter de Gruyter, New York (1979).
Teitelbaum et al., Calcifediol in Chronic Renal Insufficiency JAMA 235(2):164-167 (1976).
Teitelbaum et al., Tetracycline fluorescence in uremic and primary hyperparathyroid bone, Kidney Int., 12:366-372 (1977).
Thomas et al., Hypovitaminosis D in Medical Inpatients, NEJM, 338:777-783 (1998).
Thombre, Assessment of the feasibility of oral controlled release in an exploratory development setting, Drug Discovery Today, 10(17): 1159-1166 (2005).
Tokmak et al., High-dose cholecalciferol to correct vitamin D deficiency in haemodialysis patients, Nephrol.Dial.Transplant., 23: 4016-4020 (2008).

(56) References Cited

OTHER PUBLICATIONS

Tomida et al., Serum 25-hydroxyvitamin D as an independent determinant of 1-84 PTH and bone mineral density in non-diabetic predialysis CKD patients, Bone, 44(4):678-83 (Apr. 2009).
Trakarnvanich et al., Effect of high dose ergocalciferol in chronic kidney disease patients with 25-hydroxyvitamin D deficiency, J.Med. Assoc.Thai. 93: 885-891 (2010).
Tuohimaa et al., Both high and low levels of blood vitamin D are associated with a higher prostate cancer risk: a longitudinal, nested case-control study in the Nordic countries, Int. J. Cancer, 108(1):104-8 (2004).
US FDA Clinical Review and Evaluation of NDA for Calderol® calcifediol capsules (believed to be available circa 1983).
US FDA Summary of Basis of Approval for Calderol® calcifediol capsules (believed to be available circa 1980).
Van Weelden et al., Apoptotic Regression of MCF-7 Xenografts in Nude Mice Treated with the Vitamin $D_3$ Analog, EB1089, Endocrinology, 139:2102-2110 (1998).
Verberckmoes et al., Osteodystrophy of Dialysed Patients Treated with Vitamin D, Proc Eur Dial Transplant Assoc., 10(0): 217-226 (1973).
Vieth, Vitamin D Supplementation, 25-Hydroxyvitamin D Concentrations, and Safety, Am. J. Clin. Nutr., 69:842-856 (1999).
Vieth, What is the optimal vitamin D status for health? Prog. Biophys. Mol. Biol., 92:26-32 (2006).
Wise (ed.), Handbook of Pharmaceutical Controlled Release Technology, An Overview of Controlled Release Systems, Chapter 22, pp. 431-445, 461-463; Research and Development Aspects of Oral Controlled-Release Dosage Forms, Chapter 23, pp. 465-473, New York: Marcel Dekker, Inc. 3 (2000).
Witmer et al., Effects of 25-hydroxycholecalciferol on bone lesions of children with terminal renal failure Kidney International 10:395-408 (1976).
Wootton, Improving the Measurement of 25-Hydroxyvitamin D, Clin Biochem Rev, 26:33-36 (2005).
Written Opinion for Application No. PCT/US2007/061521, dated Jul. 17, 2007.
Written Opinion for Application No. PCT/US2008/061579, dated Aug. 21, 2008.
Yanoff et al., The Prevalence of Hypovitaminosis D and Secondary Hyperparathyroidism in Obese Black Americans, Clin. Endocrinol. (Oxf), 64(5):523-529 (2006).
Zemplar® (paricalcitol) Capsules, Final Agreed Upon Label (FDA, May 5, 2009).
Zerwekh et al., Extra-Renal Production of 24,25-Dihydroxyvitamin D in Chronic Renal Failure During 25 Hydroxyvitamin D3 Therapy, Kidney Int., 23:401-406 (1983).
Zisman et al., Impact of Ergocalciferol Treatment of Vitamin D Deficiency on Serum Parathyroid Hormone Concentrations in Chronic Kidney Disease, Am. J. Nephrol., 27:36-43 (2007).
Zucchelli et al., Therapeutic effects of 25-hydroxycholecalciferol and sodium etidronate on renal osteodystrophy, Mineral.Electrolyte Metab. 7: 86-96 (1982).
Rotuba marketing phthalate-free cellulosic, Plastic News, Nov. 26, 2007.
Yudianti et al., Effect of water soluble polymer on structure and mechanical properties of bacterial cellulose composites, J. Appl. Sci., 8(1):177-180 (2008).
Baez et al., Hipocalcemia severa posdenosumab, Nefrologfa (Madrid), 33(4): 614-615 (2013).
Gradishar et al., Minimizing cancer's impact on bone with denosumab: current and future perspectives, Community oncology, 10(8):235-243 (2013).
Sirvent et al., Extreme hypocalcaemia and hyperparathyroidism following denosumab. Is this drug safe in chronic kidney disease?, Nefrologfa (Madrid), 34(4): 542-544 (2014).
Baker et al., Plasma 25-hydroxy vitamin D concentrations in patients with fractures of the femoral neck, Br. Med. J., 1(6163):589 (1979).

9 Things That Can Undermine Your Vitamin D Level: Don't Let Your Vitamin D Absorption Slip Away, Harvard Health Publishing, downloaded from the Internet at: <https://www.health.harvard.edu/healthbeat/9-things-that-can-undermine-your-vitamin-d-level> (Feb. 11, 2019)., Feb. 11, 2019.
ACP Formulary and Pocket Guide To Psychopharmacology, Virginia DMHMRSAS, vol. 1, Iss. 1, (2004-2005).
Albertson et al., Quantitative mapping of amplicon structure by array CGH identifies CYP24 as a candidate oncogene, Nat. Genet., 25(2):144-6 (2000).
Amin, The impact of improved phosphorus control: use of sevelamer hydrochloride in patients with chronic renal failure, Nephrol Dial Transplant, 17:340-345 (2002).
Anderson et al., Expression of VDR and CYP24A1 mRNA in human tumors, Cancer Chemother. Pharmacol., 57(2):234-40 (2006).
Anderson et al., Quantification of mRNA for the vitamin D metabolizing enzymes CYP27B1 and CYP24 and vitamin D receptor in kidney using real-time reverse transcriptase-polymerase chain reaction, 2003. J. Mol. Endoc 31:123-132.
Baggiolini et al., Stereocontrolled Total Synthesis of 1 alpha, 25-Dihydroxycholecalciferol 1 and 1 alpha, 25-Dihydroxyergocalciferol, J. Org. Chem. 21:3098-3108 (1986).
Berg et al., 24,25-Dihydroxyvitamin d3 and vitamin D status of community-dwelling black and white Americans, Clin. Chem., 61(6):877-84 (Jun. 2015).
Berruti et al., Prognostic role of serum parathyroid hormone levels in advanced prostate cancer patients undergoing zoledronic acid administration, Oncologist, 17(5):645-52 (2012).
Bertoldo et al., Serum 25-hydroxyvitamin D levels modulate the acute-phase response associated with the first nitrogen-containing bisphosphonate infusion, J. Bone Miner. Res., 25(3):447-54 (Mar. 2010).
Bhatia et al., EB1089 inhibits the parathyroid hormone-related protein-enhanced bone metastasis and xenograft growth of human prostate cancer cells, Mol. Cancer Ther., 8(7):1787-98 (2009).
BioTrends Research Group, TreatmentTrends (Registered): Nephrology (US) Q4 2014 (Dec. 2014).
Boxtel et al., Drug Benefits and Risks, International Textbook of Clinical Pharmacology, p. 75-76 (2001).
Briese et al., Arterial and cardiac disease in young adults with childhood-onset end-stage renal disease-impact of calcium and vitamin D therapy, Nephrology Dialysis Transplantation., 21:1906-1914 (2006).
Brodowicz et al., Early identification and intervention matters: A comprehensive review of current evidence and recommendations for the monitoring of bone health in patients with cancer, Cancer Treat Rev., 61:23-34 (2017).
Cavalli et al., Biological effects of various regimes of 25-hydroxyvitamin D3 (calcidiol) administration on bone mineral metabolism in postmenopausal women, Clinical Cases in Mineral and Bone Metabolism, 6(2): 169-173 (2009).
Centorrino et al., Multiple versus single antipsychotic agents for hospitalized psychiatric patients: case-control study of risks versus benefits, Am J. Psychiatry, 161(4): 700-06 (2004).
Chapuy et al., Biochemical effects of calcium and vitamin D supplementation in elderly, institutionalized, vitamin D-deficient patients, Rev. Rhum. [Engl. Ed. 63 (2), 135-140), Feb. 1996.
Charnow, Novel Formulation Corrects Vitamin D, Lowers iPTH, Renal & Urology News (2012).
Chen et al., Safety of Denosumab Versus Zoledronic Acid in Patients with Bone Metastases: A Meta-Analysis of Randomized Controlled Trials, Oncol. Res. Treat., 39(7-9):453-9 (2016).
Chonchol et al., 25-Hydroxyvitamin D, insulin resistance, and kidney function in the Third National Health and Nutrition Examination Survey, Kidney Int., 71(2):134-9 (2007).
Database WPI Week 199546 Thomson Scientific, London, GB; AN 1995-355178 XP002464406.
Database WPI Week 199546 Thomson Scientific, London, GB; An 1995-355178 XP002680886.
E.W. Martin, Drug Interactions, in Hazards of Medication, J.B. Lippincott Co. (1978).

(56) References Cited

OTHER PUBLICATIONS

El Abdaimi et al., Reversal of hypercalcemia with the vitamin D analogue EB1089 in a human model of squamous cancer, Cancer Res., 59(14):3325-8 (1999).
Ennis et al., Current recommended 25-hydroxyvitamin D targets for chronic kidney disease management may be too low, J. Nephrol., 29(1):63-70 (Feb. 2016).
Epps et al., Vitamin D Metabolism: Implications for Treatment in Oncology, Oncology News, 4:42-44 (2009).
Final Office Action, U.S. Appl. No. 16/089,235, dated Dec. 10, 2019, 35 pages.
Fliser et al., Fibroblast gowth factor 23 (FGF23) predicts progression of chronic kidney disease: the mild to moderate kidney disease (MMKD) study, J. Am. Soc. Nephrol., 18:2601-8 (2007).
Fournier et al., Impact of calcium and vitamin D therapy on arterial and cardiac disease in young adults with childhood-onset and stage renal disease, Nephrol Dial Transplant , 22:956-957 (2006).
Friedrich et al., Analysis of the vitamin D system in cervical carcinomas, breast cancer and ovarian cancer, Recent Results Cancer Res., 164:239-46 (2003).
Fukagawa et al., FGF23: its role in renal bone disease, Pediatr. Nephrol., 21:1802-6 (2006).
Fukagawa et al., With or without the kidney: the role of FGF23 in CKD, Nephrol. Dial. Transplant., 20:1295-8 (2005).
Gal-Moscovici et al., Role of vitamin D deficiency in chronic kidney disease, Journal of Bone and Mineral Res. 22:V91-V94 (2007).
Garland et al., Vitamin D for cancer prevention: global perspective, Ann. Epidemiol., 19(7):468-83 (2009).
Goldzieher et al., Single-monthly-dose vitamin D supplementation in elderly patients, Endocr. Pract., 5(5):229-32 (1999).
Goodman, Calcimimetic agents and secondary hyperparathyroidism: treatment and prevention, Nephrol Dial Transplant, 2002;17:204-207.
Gopinath et al., Disintegrants—A Brief Review, J. Chem. Pharm. Sci., 5(3):105-12 (Jul.-Sep. 2012).
Guidance for Industry, Nonclinical Safety Evaluation of Drug or Biologic Combinations, U.S. Department of Health and Human Services, Food and Drug Administration (Mar. 2006).
Harris R Z et al: Pharmacokinetics of cinacalcet hydrochloride when administered with ketoconazole, Clinical Pharmacokinetics, Adis International Ltd., Auckland, NZ, vol. 46, No. 6, Jan. 1, 2007 (Jan. 1, 2007), pp. 495-501.
Heike A. A. Bischoff-Ferrari (J. of Steroid & Molecular Biology 103 (2007) 614-619).
Helvig et al., Dysregulation of renal vitamin D metabolism in the uremic rat, Kidney Int., 78(5):463-72 (2010).
Hemodialysis (2015, 4 pages, Accessed from https://www.kidney.org/atoz/content/hemodialysis on Jun. 19, 2019) (Year: 2015).
Henry et al., Response of chick parathyroid glands to the vitamin D metabolites, 1,25-dihydroxycholecalciferol and 24,25-dihydroxycholecalciferol, J. Nutr., 107(10):1918-26 (1977).
Holick et al., Vitamin D2 is as effective as vitamin D3 in maintaining circulating concentrations of 25-dydroxyvitamin D, J Clin Endocrinol Metab., 93(3):677-81 (2008).
Holick et al., Evaluation, treatment, and prevention of vitamin D deficiency: an Endocrine Society clinical practice guideline, J. Clin. Endocrinol. Metab., 96(7):1911-30 (Jul. 2011).
Holick, Vitamin D for health and in chronic kidney disease, Semin. Dial., 18(4):266-75 (2005).
Ibrahim et al., Serum fibroblast growth factor-23 levels in chronic haemodialysis patients, Int. Urol. Nephrol., 41:163-9 (2009).
Inoue et al., Role of the vitamin D receptor in FGF23 action on phosphate metabolism, Biochem. J., 399:325-31 (2005).
International Preliminary Report on Patentability for Corresponding International Application No. PCT/EP17/57282, dated Oct. 11, 2018, 7 pages.
International Preliminary Report on Patentability for Corresponding International Application No. PCT/US09/39355, dated Oct. 14, 2010, 8 pages.
Jones et al., Cytochrome P450-mediated metabolism of vitamin D, J. Lipid Res., 55(1):13-31 (2014).
Jones, Why dialysis patients need combination therapy with both cholecalciferol and a calcitriol analogs, Seminars in Di alysis, pp. 1-5 (2010).
Kaufmann et al. J. Clin. Endocrinol. Metab., 2014, vol. 99, pp. 2567-2574 (Year: 2014).
Kaufmann et al., Clinical utility of simultaneous quantitation of 25-hydroxyvitamin D and 24,25-dihydroxyvitamin D by LC-MS/MS involving derivatization with DMEQ-TAD, J. Clin. Endocrinol. Metab., 99(7):2567-74 (Jul. 2014).
Kazama et al., Role of circulating fibroblast growth factor 23 in the development of secondary hyperparathyroidism, Ther. Apher. Dial., 9:328-30 (2005).
KDOQI Clinical practice guidelines 2004. National Kidney Foundation).
Kidney Disease Improving Global Outcomes (KDIGO) Clinical Practice Guidelines for Diagnosis, Evaluation, Prevention, and Treatment of Chronic Kidney Disease-Mineral and Bone Disorder (CKD-MBD), Kidney International Supplement, 113:S1-130 (2009).
Krishnan et al., The role of vitamin Din cancer prevention and treatment, Rheum. Dis. Clin. North Am., 38(1):161-78 (2012).
KURO-O, Klotho in chronic kidney disease—what's new?, Nephrol. Dial. Transplant., 4 pp. (2009).
Luo et al., 24-Hydroxylase in cancer: impact on vitamin D-based anticancer therapeutics, J. Steroid Biochem. Mal. Biol., 136:252-7 (2013).
Martin-Baez et al., Severe hypocalcaemia post-denosumab, Nefrologia, 33(4):614-5 (2013).
Joy et al: Outcomes of Secondary Hyperparathyroidism in Chronic Kidney Disease and the Direct Costs of Treatment, Journal of Managed Care Pharmacy, Academy of, Managed Care Pharmacy, Alexandria, VA, vol. 13, No. 5, Jan. 1, 2007 (Jan. 1, 2007), pp. 397-411.
Holick, Vitamin D: A millenium perspective, J. Cell Biochem.. 88:296-307 (2003).
Mimori et al., Clinical significance of the overexpression of the candidate oncogene CYP24 in esophageal cancer, Ann. Oncol., 15(2):236-41 (2004).
Motellon et al., Parathyroid hormone-related protein, parathyroid hormone, and vitamin Din hypercalcemia of malignancy, Clin. Chim. Acta, 290(2):189-97 (2000).
NASMHPD Medical Director's Technical Report on Psychiatric Polypharmacy (Sep. 2001).
National Kidney Foundation Guidelines, NKF, Am. J. Kidney Dis., 42(4, Suppl 3):S1-5202 (2003).
NewsWire (https://www.newswire.ca/news-releases/cytochroma-announces-data-presentations-at-american-society-of-hephrologys43rd-annual-meeting-and-scientific-exposition-546289852.html, published Nov. 18, 2010) (Year: 2010).
NewsWire (https://www.newswire.ca/news-releases/cytochroma-announces-data-presentations-at-american-society-of-nephrologys43rd-annual-meeting-and-scientfflc-exposition-546289852.html. published Nov. 18, 2010) (Year: 2010).
Non-Final Office Action received for U.S. Appl. No. 12/597,230, dated Dec. 13, 2019, 15 pages.
Notice of Allowance, U.S. Appl. No. 15/918,620, dated Nov. 29, 2019, 9 pages.
Olmos et al., Effects of 25-hydroxyvitamin D3 therapy on bone turnover markers and PTH levels in postmenopausal osteoporotic women treated with alendronate, J. Clin. Endocrinol. Metab., 97(12):4491-7 (2012).
OPKO Health Inc., Safety/Efficacy Study of CTAP101 in Chronic Kidney Disease Subjects With Secondary Hyperparathyroidism (SHPT), <https://clinicaltrials.govict2/show/NCT01219855> Oct. 13, 2010.
Package insert for Hectorol (doxercalciferol capsules), Genzyme (2011).
Package insert for Zemplar (paricalcitol) Capsules, Abbott (2011).
Pak et al., Treatment of Vitamin D-Resistant Rickets With 25-Hydroxycholecalciferol, Arch Intern Med, 129:894-899 (1972).

(56) References Cited

OTHER PUBLICATIONS

Parise et al., CYP24, the enzyme that catabolizes the antiproliferative agent vitamin D, is increased in lung cancer, Int. J. Cancer, 119(8):1819-28 (2006).
Petkovich et al., CYP24A1 and Kidney Disease, Current Opin. in Nephrology and Hypertension, 20:337-344 (2011).
Posner et al., Vitamin D Analogues Targeting CYP24 in Chronic Kidney Disease, J. Steroid Biochem and Mol. Biol., 121:13-19 (2010).
Rabbani, Molecular mechanism of action of parathyroid hormone related peptide in hypercalcemia of malignancy: therapeutic strategies (review), Int. J. Oncol., 16(1):197-206 (2000).
Richard et al., PTHrP gene expression in cancer: do all paths lead to Ets?, Crit. Rev. Eukaryot. Gene Expr., 15(2):115-32 (2005).
Rocaltrol (Registered) Complete Product Information, Roche, Jul. 27, 2004.
Saseen et al., Dual calcium-channel blocker therapy in the treatment of hypertension, Ann Pharmacother., 30(7-8): 802-10 (1996).
Sato et al., Increased 1,25-(OH)2D2 concentration in a patient with malignancy-associated hypercalcemia receiving intravenous hyperalimentation inadvertently supplemented with vitamin D2, Intern. Med., 32(11):886-90 (1993).
Schwartz et al., Extended-release calcifediol (ERC) effectively increased serum 25-hydroxyvitamin D levels in breast and prostate cancer patients without significant impact on serum calcium or phosphorus, Opko Renal (2018).
Segersten et al.: Potentiating effects of nonactive/active vitamin D analogues and ketoconazole in parathyroid cells, Clinical Endocrinology., vol. 66, No. 3, Mar. 1, 2007 (Mar. 1, 2007), pp. 399-404.
Sensipar (cinacalcet) prescriptioninformation, revised Aug. 2011.
Sensipar package insert (Year: 2004).
Sicinski et al., Synthesis of 1 alpha, 25-Dihydroxyvitamin D2, Its 24 Epimer and Related Isomers, and Their Binding Affinity for the 1, 25-Dihydroxyvitamin D3 Receptor, Bioorganic Chemistry, 13:158-169 (1985).
Skugor M. et al.: Evolution and current state of assays for parathyriod hormone, Biochemia Medica, vol. 20, No. 2, 2010, pp. 221-228.
Soyfoo et al., Non-malignant causes of hypercalcemia in cancer patients: a frequent and neglected occurrence, Support Care Cancer, 21(5):1415-9 (2013).
Sprague et al., Modified-release calcifediol effectively controls secondary hyperparathyroidism associated with vitamin D insufficiency in chronic kidney disease, Am. J. Nephrol., 40(6):535-45 (2015).
Sprague et al., Use of Extended-Release Calcifediol to Treat Secondary Hyperparathyroidism in Stages 3 and 4 Chronic Kidney Disease, Am. J. Nephrol., 44(4):316-25 (2016).
Tebben et al., Elevated fibroblast growth factor 23 in women with malignant ovarian tumors, Mayo Clin. Proc., 80:745-51 (2005).
Terrie, Monitoring Combination Drug Therapy, Pharmacy Times, published Jan. 18, 2010., Jan. 19, 2010,.
Tsuji, et al. A New and Convenient Synthesis of 1α,25-Dihydroxyvitamin D2 and It 24R-Epimer, Bull. Chem. Soc. Jpn., 62:10 pp. 3132-3137 (1989).
Wagner et al., The ratio of serum 24,25-dihydroxyvitamin D(3) to 25-hydroxyvitamin D(3) is predictive of 25-hydroxyvitamin D(3) response to vitamin D(3) supplementation, J. Steriod Biochem. Mal. Biol., 126(3-5):72-7 (Sep. 2011).
Wang-Gillam et al., Evaluation of vitamin D deficiency in breast cancer patients on bisphosphonates, Jul. 1, 2008, Oncologist, 821-7, 13(7).
Yueh-Ting et al: Comparison between Calcitriol and Caltiriol Plus Low-Dose Cinacalcet for the Treatment of Moderate to Severe Secondary Hyperparathyroidism in Nutrients, vol. 5, No. 4, Apr. 19, 2013 (apr. 19, 2013), pp. 1336-1348.
Zerwekh J. E .: Blood biomarkers of vitamin D status, The American Journal of Clinical Nutrition, vol. 87Suppl., 2008, pp. 1087S-1091S.
Zuradelli et al., High incidence of hypocalcemia and serum creatinine increase in patients with bone metastases treated with zoledronic acid, Oncologist, 14(5):548-56 (2009).

* cited by examiner

TREATING VITAMIN D INSUFFICIENCY AND DEFICIENCY WITH 25-HYDROXYVITAMIN $D_2$ AND 25-HYDROXYVITAMIN $D_3$

This is a continuation of U.S. patent application Ser. No. 16/171,100, filed Oct. 25, 2018, which is a continuation of U.S. patent application Ser. No. 15/722,757, filed Oct. 2, 2017, now U.S. Pat. No. 10,213,442, issued Feb. 26, 2019, which is a continuation of U.S. patent application Ser. No. 14/548,275, filed Nov. 19, 2014, now U.S. Pat. No. 9,943,530, issued Apr. 17, 2018, which is a continuation of U.S. patent application Ser. No. 13/848,982 filed Mar. 22, 2013, now U.S. Pat. No. 8,906,410, issued Dec. 9, 2014, which is a divisional of U.S. patent application Ser. No. 12/278,053, filed Feb. 23, 2009, now U.S. Pat. No. 8,426,391, issued Apr. 23, 2013, which is the National Phase of International Application No. PCT/US2007/061521, filed Feb. 2, 2007, which claims the benefit of priority under 35 U.S.C. § 119(e) of U.S. Provisional Patent Application No. 60/764,665, filed Feb. 3, 2006. The disclosure of each priority application is incorporated herein by reference.

BACKGROUND

The Vitamin D metabolites known as 25-hydroxyvitamin $D_2$ and 25-hydroxyvitamin $D_3$ (collectively referred to as "25-hydroxyvitamin D") are fat-soluble steroid prohormones to Vitamin D hormones that contribute to the maintenance of normal levels of calcium and phosphorus in the bloodstream. The prohormone 25-hydroxyvitamin $D_2$ is produced from Vitamin $D_2$ (ergocalciferol) and 25-hydroxyvitamin $D_3$ is produced from Vitamin $D_3$ (cholecalciferol) primarily by one or more enzymes located in the liver. The two prohormones also can be produced outside of the liver from Vitamin $D_2$ and Vitamin $D_3$ (collectively referred to as "Vitamin D") in certain cells, such as enterocytes, which contain enzymes identical or similar to those found in the liver.

The prohormones are further metabolized in the kidneys into potent hormones. The prohormone 25-hydroxyvitamin $D_2$ is metabolized into a hormone known as 1α,25-dihydroxyvitamin $D_3$; likewise, 25-hydroxyvitamin $D_3$ is metabolized into 1α,25-dihydroxyvitamin $D_3$ (calcitriol). Production of these hormones from the prohormones also can occur outside of the kidney in cells which contain the required enzyme(s).

The Vitamin D hormones have essential roles in human health which are mediated by intracellular Vitamin D receptors (VDR). In particular, the Vitamin D hormones regulate blood calcium levels by controlling the absorption of dietary calcium by the small intestine and the reabsorption of calcium by the kidneys. Excessive hormone levels, whether transient or prolonged, can lead to abnormally elevated urine calcium (hypercalciuria), blood calcium (hypercalcemia) and blood phosphorus (hyperphosphatemia). The Vitamin D hormones also participate in the regulation of cellular differentiation and growth, PTH secretion by the parathyroid glands, and normal bone formation and metabolism. Further, Vitamin D hormones are required for the normal functioning of the musculoskeletal, immune and renin-angiotensin systems. Numerous other roles for Vitamin D hormones are being postulated and elucidated, based on the documented presence of intracellular VDR in nearly every human tissue.

The actions of Vitamin D hormones on specific tissues depend on the degree to which they bind to (or occupy) the intracellular VDR in those tissues. The prohormones 25-hydroxyvitamin $D_2$ and 25-hydroxyvitamin $D_3$ have essentially identical affinities for the VDR which are estimated to be at least 100-fold lower than those of the Vitamin D hormones. As a consequence, physiological concentrations of 25-hydroxyvitamin $D_2$ and 25-hydroxyvitamin $D_3$ have little, if any, biological actions without prior metabolism to Vitamin D hormones. However, supraphysiologic levels of 25-hydroxyvitamin $D_2$ and 25-hydroxyvitamin $D_3$, in the range of 10 to 1,000 fold higher than normal, can sufficiently occupy the VDR to exert actions like the Vitamin D hormones.

Surges in blood or intracellular prohormone concentrations can promote excessive extrarenal hormone production, leading to local adverse effects on calcium and phosphorus metabolism. They also can inhibit hepatic prohormone production from Vitamin D, and promote catabolism of both Vitamin D and 25-hydroxyvitamin D in the kidney and/or other tissues. Blood levels of both the prohormones and the Vitamin D hormones are normally constant through the day, given a sustained, adequate supply of Vitamin D from sunlight exposure or an unsupplemented diet. Blood levels of 25-hydroxyvitamin D, however, can increase markedly after administration of currently available Vitamin D supplements, especially at doses which greatly exceed the minimum amounts required to prevent Vitamin D deficiency rickets or osteomalacia. Prohormone blood levels can also increase markedly after rapid intravenous administration of 25-hydroxyvitamin $D_2$ and/or 25-hydroxyvitamin $D_3$.

Production of 25-hydroxyvitamin $D_2$ and 25-hydroxyvitamin $D_3$ declines when Vitamin D is in short supply, as in conditions such as Vitamin D insufficiency or Vitamin D deficiency (alternatively, hypovitaminosis D). Low production of 25-hydroxyvitamin $D_2$ and 25-hydroxyvitamin $D_3$ leads to low blood levels of 25-hydroxyvitamin D. Inadequate Vitamin D supply often develops in individuals who are infrequently exposed to sunlight without protective sunscreens, have chronically inadequate intakes of Vitamin D, or suffer from conditions that reduce the intestinal absorption of fat soluble vitamins (such as Vitamin D). It has recently been reported that most individuals living in northern latitudes have inadequate Vitamin D supply. Left untreated, inadequate Vitamin D supply can cause serious bone disorders, including rickets and osteomalacia, and may contribute to the development of many other disorders including osteoporosis, non-traumatic fractures of the spine and hip, obesity, diabetes, muscle weakness, immune deficiencies, hypertension, psoriasis, and various cancers.

The Institute of Medicine (TOM) of the National Academy of Sciences has concluded that an Adequate Intake (AI) of Vitamin D for a healthy individual ranges from 200 to 600 IU per day, depending on the individual's age and sex [Standing Committee on the Scientific Evaluation of Dietary Reference Intakes, *Dietary reference intakes: calcium, phosphorus, magnesium, vitamin D, and fluoride*. Washington, DC: National Academy Press (1997)], incorporated by reference. The AI for Vitamin D was defined primarily on the basis of a serum 25-hydroxyvitamin D level sufficient to prevent Vitamin D deficiency rickets or osteomalacia (or >11 ng/mL). The TOM also established a Tolerable Upper Intake Level (UL) for Vitamin D of 2,000 IU per day, based on evidence that higher doses are associated with an increased risk of hypercalciuria, hypercalcemia and related sequelae, including cardiac arrhythmias, seizures, and generalized vascular and other soft-tissue calcification.

Currently available oral Vitamin D supplements are far from ideal for achieving and maintaining optimal blood 25-hydroxyvitamin D levels. These preparations typically contain 400 IU to 5,000 IU of Vitamin $D_3$ or 50,000 IU of Vitamin $D_2$ and are formulated for quick or immediate release in the gastrointestinal tract. When administered at chronically high doses, as is often required for Vitamin D repletion, these products have significant and, often, severe limitations which are summarized below.

High doses of immediate release Vitamin D supplements produce marked surges in blood Vitamin D levels, thereby promoting: (a) storage of Vitamin D in adipose tissue, which is undesirable because stored Vitamin D is less available for later conversion to 25-hydroxyvitamin D; (b) catabolism of Vitamin D to metabolites which are less or no longer useful for boosting blood 25-hydroxyvitamin D levels, via 24- and/or 26-hydroxylation; and, (c) excessive intracellular 24- or 25-hydroxylation of Vitamin D, which leads to increased risk of hypercalciuria, hypercalcemia and hyperphosphatemia via mass-action binding to the VDR.

High doses of immediate release Vitamin D supplements also produce surges or spikes in blood and intracellular 25-hydroxyvitamin D levels, thereby promoting: (a) transiently excessive renal and extrarenal production of Vitamin D hormones, and leading to local aberrations in calcium and phosphorus homeostasis and increased risk of hypercalciuria, hypercalcemia and hyperphosphatemia; (b) catabolism of both Vitamin D and 25-hydroxyvitamin D by 24-and/or 26-hydroxylation in the kidney and other tissues; (c) down-regulation of hepatic production of Vitamin D prohormones, unnecessarily impeding the efficient repletion of Vitamin D insufficiency or deficiency; and, (d) local aberrations in calcium and phosphorus homeostasis mediated by direct binding to VDR.

Furthermore, high doses of immediate release Vitamin D supplements produce supraphysiologic, even pharmacological, concentrations of Vitamin D, e.g., in the lumen of the duodenum, promoting: (a) 25-hydroxylation in the enterocytes and local stimulation of intestinal absorption of calcium and phosphorus, leading to increased risk of hypercalciuria, hypercalcemia and hyperphosphatemia; and (b) catabolism of Vitamin D by 24- and 26-hydroxylation in the local enterocytes, causing decreased systemic bioavailability.

Vitamin D supplementation above the UL is frequently needed in certain individuals; however, currently available oral Vitamin D supplements are not well suited for maintaining blood 25-hydroxyvitamin D levels at optimal levels given the problems of administering high doses of immediate release Vitamin D compounds.

Administration of 25-hydroxyvitamin $D_3$ in an immediate release oral formulation has been tried as an alternative method of Vitamin D supplementation. This approach, which has been subsequently abandoned, caused problems as do the currently used Vitamin D supplements. Specifically, it produced surges or spikes in blood and intracellular D levels, thereby promoting (a) competitive displacement of Vitamin D hormones from the serum Vitamin D Binding Protein (DBP) and excessive delivery of the displaced hormones to tissues containing VDR, and (b) transiently excessive renal and extrarenal production of Vitamin D hormones, which together led to local aberrations in calcium and phosphorus metabolism. In addition, these surges in blood 25-hydroxyvitamin D levels promoted catabolism of both Vitamin D and 25-hydroxyvitamin D by 24- and/or 26-hydroxylation in the kidney and other tissues, down-regulation of hepatic production of Vitamin D prohormones, unnecessarily impeding the efficient repletion of Vitamin D insufficiency or deficiency, and, additional local aberrations in calcium and phosphorus homeostasis mediated by direct binding to VDR. Importantly, immediate release 25-hydroxyvitamin $D_3$ promoted its intestinal absorption via a mechanism substantially involving transport to the liver in chylomicrons, rather than bound to the serum DBP. Delivery of 25-hydroxyvitamin D to the liver via chylomicrons significantly increased the likelihood of its catabolism.

Clearly, an alternative approach to Vitamin D supplementation is needed given the problems encountered with both currently available oral Vitamin D supplements, and with previously used oral 25-hydroxyvitamin $D_3$.

SUMMARY OF THE INVENTION

The present invention provides methods for effectively and safely restoring blood 25-hydroxyvitamin D levels to optimal levels (defined for patients as >30 ng/mL 25-hydroxyvitamin D) and maintaining blood 25-hydroxyvitamin D levels at such optimal levels. The method includes dosing a subject, an animal or a human patient, orally or intravenously with sufficient 25-hydroxyvitamin $D_2$ or 25-hydroxyvitamin $D_3$ or any combination of these two prohormones in a formulation that provides benefits to the recipient that were heretofore unimagined with currently available Vitamin D supplements. That is, the present invention provides effective Vitamin D supplementation that reduces the risk of transient surges (i.e., supraphysiologic levels) of blood 25-hydroxyvitamin D and related side effects.

In an embodiment of the present invention, an amount of 25-hydroxyvitamin $D_2$ and/or 25-hydroxyvitamin $D_3$ is included in a controlled release formulation and is orally administered daily to a human or animal in need of treatment. In another embodiment, an amount of 25-hydroxyvitamin $D_2$ and/or 25-hydroxyvitamin $D_3$ is included in an isotonic sterile formulation suitable for intravenous administration, and is gradually injected thrice weekly into a human or animal in need of treatment. This administration of 25-hydroxyvitamin $D_2$ and/or 25-hydroxyvitamin $D_3$ significantly: increases the bioavailability of the contained 25-hydroxyvitamin $D_2$/25-hydroxyvitamin $D_3$; decreases the undesirable first pass effects of the contained 25-hydroxyvitamin $D_2$/25-hydroxyvitamin $D_3$ on the duodenum; avoids producing supraphysiologic surges in blood levels of 25-hydroxyvitamin $D_2$ and/or 25-hydroxyvitamin $D_3$; increases the effectiveness of orally administered 25-hydroxyvitamin $D_2$/25-hydroxyvitamin $D_3$ in restoring blood concentrations of 25-hydroxyvitamin D to optimal levels (defined for patients as >30 ng/mL 25-hydroxyvitamin D); increases the effectiveness of orally administered 25-hydroxyvitamin $D_2$/25-hydroxyvitamin $D_3$ in maintaining blood concentrations of 25-hydroxyvitamin D at such optimal levels; decreases disruptions in Vitamin D metabolism and related aberrations in PTH, calcium and phosphorus homeostasis; and, decreases the risk of serious side effects associated with Vitamin D supplementation, namely Vitamin D toxicity.

In one aspect, the present invention provides a stable controlled release composition comprising 25-hydroxyvitamin $D_2$ and/or 25-hydroxyvitamin $D_3$, which is formulated to allow the 25-hydroxyvitamin D to pass through the stomach, and the duodenum and jejunum of the small intestine, to the ileum. The composition effectively resists disintegration in gastric juice, and avoids substantial release of the contained 25-hydroxyvitamin D until it reaches the ileum of the small intestine, thereby minimizing absorption substantially mediated by transport to the liver in chylomicrons. The disclosed composition is gradually presented to the intralumenal and intracelulluar aspects of the ileum, reducing CYP24-mediated catabolism and provoking a sustained increase in the blood levels of 25-hydroxyvitamin D to optimal levels which can be maintained.

In another aspect, the invention provides an isotonic sterile formulation suitable for gradual intravenous administration containing 25-hydroxyvitamin $D_2$ and/or 25-hydroxyvitamin $D_3$, which allows the 25-hydroxyvitamin D to completely bypass the gastrointestinal tract, thereby eliminating first pass effects on the duodenum and jejunum, as well as absorption mediated by transport to the liver in chylomicrons.

The foregoing brief description has outlined, in general, the featured aspects of the invention and is to serve as an aid to better understanding the more complete detailed description which is to follow. In reference to such, there is to be a clear understanding that the present invention is not limited to the method or detail of manufacture, chemical composition, or application of use described herein. Any other variation of manufacture, chemical composition, use, or application should be considered apparent as an alternative embodiment of the present invention. Other advantages and a fuller appreciation of the specific adaptations, compositional variations and chemical and physical attributes of this invention will be gained upon examination of the detailed description.

Also, it is understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

DETAILED DESCRIPTION OF THE INVENTION

The present invention relates to a method for dosing a subject, an animal or a human patient, in need of Vitamin D supplementation with sufficient 25-hydroxyvitamin $D_2$, 25-hydroxyvitamin $D_3$ or any combination of these two prohormones to effectively and safely restore blood 25-hydroxyvitamin D levels to optimal levels (defined for human subjects and patients as >30 ng/mL 25-hydroxyvitamin D) and to maintain blood 25-hydroxyvitamin D levels at such optimal levels.

As used herein, the following definitions may be useful in aiding the skilled practitioner in understanding the invention:

As used herein, the term "substantially constant" with respect to the serum or blood level of 25-hydroxyvitamin D means that the release profile of any formulation administered as detailed hereinbelow should not include transient increases in total serum or blood levels of 25-hydroxyvitamin $D_3$ or 25-hydroxyvitamin $D_2$ of greater than approximately 3 ng/mL after administration of a unit dose.

As used herein, the term "controlled release" and "sustained release" are used interchangeably, and refer to the release of the administered 25-hydroxyvitamin D at such a rate that total serum or blood levels of 25-hydroxyvitamin D are maintained or elevated above predosing levels for an extended period of time, e.g., 4 to 24 hours or even longer.

As used herein, the term "Vitamin D toxicity" is meant to refer to the side effects suffered from excessive administration of 25-hydroxyvitamin D and excessively elevated 25-hydroxyvitamin D blood levels, including nausea, vomiting, polyuria, hypercalciuria, hypercalcemia and hyperphosphatemia.

"Suprapysiologic" in reference to intralumenal, intracelulluar and blood concentrations of 25-hydroxyvitamin D refers to a combined concentration of 25-hydroxyvitamin $D_2$ and 25-hydroxyvitamin $D_3$ during a 24-hour post-dose period which is more than 5 ng/mL greater than the generally stable levels observed over the course of the preceding 24-hour period by laboratory measurement.

"Vitamin D insufficiency and deficiency" is generally defined as having serum 25-hydroxyvitamin D levels below 30 ng/mL (National Kidney Foundation guidelines, NKF, *Am. J. Kidney Dis.* 42:S1-S202 (2003), incorporated herein by reference).

Unless indicated otherwise, "25-hydroxyvitamin $D_2$/25-hydroxyvitamin $D_3$" as used herein is intended to encompass 25-hydroxyvitamin $D_2$, 25-hydroxyvitamin $D_3$, or a combination thereof.

Unless indicated otherwise, "25-hydroxyvitamin D" is intended to refer to 25-hydroxyvitamin $D_2$ and 25-hydroxyvitamin $D_3$ collectively. For example, an assayed blood level of 25-hydroxyvitamin D will include both 25-hydroxyvitamin $D_2$ and 25-hydroxyvitamin $D_3$, if present.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

The invention includes compositions comprising oral and intravenous formulations of 25-hydroxyvitamin $D_2$ and/or 25-hydroxyvitamin $D_3$ and methods of administering such formulations to treat 25-hydroxyvitamin D insufficiency and deficiency without the potential first pass effects of these prohormones on the duodenum and jejunum; without supraphysiological surges in intralumenal, intracellular and blood levels of 25-hydroxyvitamin D and their consequences; without causing substantially increased catabolism of the administered 25-hydroxyvitamin D; and, without causing serious side effects associated with Vitamin D supplementation, namely Vitamin D toxicity.

The controlled release compositions intended for oral administration in accordance with the present invention are designed to contain concentrations of the 25-hydroxyvitamin $D_2$/25-hydroxyvitamin $D_3$ of 1 to 50 mcg per unit dose, and are prepared in such a manner as to effect controlled or substantially constant release of the 25-hydroxyvitamin $D_2$/25-hydroxyvitamin $D_3$ into the ileum of the gastrointestinal tract of humans or animals over an extended period of time. The compositions ensure a (a) substantially increased absorption of 25-hydroxyvitamin D via transport on DBP and decreased absorption via transport in chylomicrons, and (b) maintenance of substantially constant blood levels of 25-hydroxyvitamin D during the 24-hour post-dosing period. By providing a gradual, sustained and direct release of the 25-hydroxyvitamin $D_2$/25-hydroxyvitamin $D_3$ preferentially to circulating DBP (rather than to chylomicrons), blood, intralumenal and intracellular 25-hydroxyvitamin D concentration spikes, i.e., suprapysiologic levels and related unwanted catabolism are mitigated or eliminated.

The compositions intended for intravenous administration in accordance with the present invention are designed to contain concentrations of the 25-hydroxyvitamin $D_2$/25-hydroxyvitamin $D_3$ of 1 to 25 mcg per unit dose, and are prepared in such a manner as to allow gradual injection, over a period of 1 to 5 minutes, to effect controlled or substantially constant release of the 25-hydroxyvitamin $D_2$/25-hydroxyvitamin $D_3$ directly to DBP in the blood. The compositions ensure complete bioavailability of the administered 25-hydroxyvitamin D, complete elimination of first pass effects on the duodenum and jejunum, decreased catabolism of 25-hydroxyvitamin D, and maintenance of substantially constant blood levels of 25-hydroxyvitamin D during the 24-hour post-dosing period. By providing a gradual, sustained and direct release of the 25-hydroxyvitamin $D_2$/25-hydroxyvitamin $D_3$ over time to circulating DBP, intralumenal, intracellular and even blood 25-hydroxyvitamin D concentration spikes, i.e., supraphysiologic levels, are mitigated or eliminated.

The compositions of the present invention comprise highly stable pharmaceutical formulations into which 25-hydroxyvitamin $D_2$ and/or 25-hydroxyvitamin $D_3$ is incorporated for convenient daily oral administration. The disclosed compositions produce gradual increases in and then sustained blood levels of 25-hydroxyvitamin D with dual unexpected benefits with continued regular administration over a prolonged period of time of unsurpassed effectiveness in restoring blood 25-hydroxyvitamin D to optimal levels, and unsurpassed safety relative to heretofore known formulations of Vitamin D or 25-hydroxyvitamin D.

The preparation of a controlled, substantially constant release form of 25-hydroxyvitamin $D_2$/25-hydroxyvitamin $D_3$ suitable for oral administration can be carried out according to many different techniques. For example, the 25-hydroxyvitamin $D_2$/25-hydroxyvitamin $D_3$ can be dispersed within a matrix, i.e. a unique mixture of rate controlling constituents and excipients in carefully selected ratios within the matrix, and encased with a coating material. Various coating techniques can be utilized to control the rate and/or the site of the release of the 25-hydroxyvitamin $D_2$/25-hydroxyvitamin $D_3$ from the pharmaceutical formulation. For example, the dissolution of the coating may be triggered by the pH of the surrounding media, and the resulting gradual dissolution of the coating over time exposes the matrix to the fluid of the intestinal environment. After the coating becomes permeable, 25-hydroxyvitamin $D_2$/25-hydroxyvitamin $D_3$ diffuses from the outer surface of the matrix. When this surface becomes exhausted or depleted of 25-hydroxyvitamin $D_2$/25-hydroxyvitamin $D_3$, the underlying stores begin to be depleted by diffusion through the disintegrating matrix to the external solution.

In one aspect, a formulation in accordance with the present invention provides 25-hydroxyvitamin $D_2$ and/or 25-hydroxyvitamin $D_3$ within a matrix that releasably binds the ingredients in a controlled substantially constant release when exposed to the contents of the ileum.

The 25-hydroxyvitamin $D_2$ and/or 25-hydroxyvitamin $D_3$ containing matrix is suitably covered with a coating that is resistant to disintegration in gastric juices. The coated controlled release formulation of 25-hydroxyvitamin $D_2$/25-hydroxyvitamin $D_3$ is then administered orally to subjects, e.g., animals or human subjects and patients. As the formulation travels through the proximal portion of the small intestine, the enteric coating becomes progressively more permeable but, in a suitable embodiment, it provides a persisting structural framework around the 25-hydroxyvitamin $D_2$ and/or 25-hydroxyvitamin $D_3$ containing matrix. The 25-hydroxyvitamin $D_2$ and/or 25-hydroxyvitamin $D_3$ containing matrix becomes significantly exposed to intestinal fluids in the ileum through the permeable overcoating, and the 25-hydroxyvitamin $D_2$/25-hydroxyvitamin $D_3$ is then gradually released by simple diffusion and/or slow disintegration of the matrix.

Once released into the lumen of the ileum, the 25-hydroxyvitamin $D_2$/25-hydroxyvitamin $D_3$ is absorbed into the lymphatic system or into the portal bloodstream where it is bound to and transported by the DBP. The major portion of 25-hydroxyvitamin $D_2$/25-hydroxyvitamin $D_3$ is absorbed at a point beyond the duodenum and jejunum. These proximal portions of the small intestine can respond to high intralumenal levels of 25-hydroxyvitamin $D_2$/25-hydroxyvitamin $D_3$ and, in the process, can catabolize significant quantities of the 25-hydroxyvitamin $D_2$/25-hydroxyvitamin $D_3$. By substantially delaying 25-hydroxyvitamin $D_2$/25-hydroxyvitamin $D_3$ release until the ileum, the pharmaceutical composition described herein virtually eliminates these potential first pass effects on the proximal intestine, and reduces unwanted catabolism. Significant catabolism of administered Vitamin D prior to its absorption into the bloodstream significantly lowers its bioavailability. Elimination of first pass effects reduces the risk of Vitamin D toxicity. Substantially delayed release of 25-hydroxyvitamin D (i.e., beyond the duodenum and jejunum) markedly decreases the amount of 25-hydroxyvitamin D that is incorporated and absorbed from the small intestine via chylomicrons (since chylomicron formation and absorption occurs primarily in the jejunum) and correspondingly increases the amount of 25-hydroxyvitamin D that is absorbed directly through the intestinal wall and onto DBP circulating in lymph or portal blood.

In one embodiment of the invention, the controlled release oral formulation of $D_2$ and/or 25-hydroxyvitamin $D_3$ is prepared generally according to the following procedure. A sufficient quantity of 25-hydroxyvitamin $D_2$ and/or 25-hydroxyvitamin $D_3$ is completely dissolved in a minimal volume of USP-grade absolute ethanol (or other suitable solvent) and mixed with appropriate amounts and types of pharmaceutical-grade excipients to form a matrix which is solid or semi-solid at both room temperature and at the normal temperature of the human body. The matrix is completely or almost entirely resistant to digestion in the stomach and upper small intestine, and it gradually disintegrates in the lower small intestine.

In a suitable formulation, the matrix binds the 25-hydroxyvitamin $D_2$ and/or $D_3$ and permits a slow, relatively steady, i.e., substantially constant, release of the 25-hydroxyvitamin $D_2$/25-hydroxyvitamin $D_3$ over a period of four to eight hours or more, by simple diffusion and/or gradual disintegration, into the contents of the lumen of the lower small intestine. The formulation further has an enteric coating that partially dissolves in aqueous solutions having a pH of about 7.0 to 8.0, or simply dissolves slowly enough that significant release of 25-hydroxyvitamin $D_2$/25-hydroxyvitamin $D_3$ is delayed until after the formulation passes through the duodenum and jejunum.

As discussed above, the means for providing the controlled release of 25-hydroxyvitamin $D_2$ and/or 25-hydroxyvitamin $D_3$ may be selected from any of the known controlled release delivery systems of an active ingredient over a course of about four or more hours including the wax matrix system, and the Eudragit RS/RL system (of Rohm Pharma, GmbH, Weiterstadt, Germany).

The wax matrix system provides a lipophilic matrix. The wax matrix system may utilize, beeswax, white wax, cachalot wax or similar compositions. The active ingredient(s) are dispersed in the wax binder which slowly disintegrates in intestinal fluids to gradually release the active ingredient(s). The wax binder that is impregnated with the 25-hydroxyvitamin $D_2$ and/or 25-hydroxyvitamin $D_3$ is loaded into partially crosslinked soft gelatin capsules. The wax matrix system disperses the active ingredient(s) in a wax binder which softens at body temperature and slowly disintegrates in intestinal fluids to gradually release the active ingredient(s). The system suitably includes a mixture of waxes, with the optional addition of oils, to achieve a melting point which is higher than body temperature but lower than the melting temperature of gelatin formulations typically used to create the shells of either soft and hard gelatin capsules or other formulations used to create enteric coatings.

Specifically, in one suitable embodiment, the waxes selected for the matrix are melted and thoroughly mixed. The desired quantity of oils are added at this time, followed by sufficient mixing. The waxy mixture is then gradually cooled to a temperature just above its melting point. The desired amount of 25-hydroxyvitamin $D_2$ and/or 25-hydroxyvitamin $D_3$, dissolved in ethanol, is uniformly distributed into the molten matrix, and the matrix is loaded into soft gelatin capsules. The filled capsules are treated for appropriate periods of time with a solution containing an aldehyde, such as acetaldehyde, to partially crosslink the gelatin in the capsule shell. The gelatin shell becomes increasingly crosslinked, over a period of several weeks and, thereby, more resistant to dissolution in the contents of stomach and upper intestine. When properly constructed, this gelatin shell will gradually dissolve after oral administration and become sufficiently porous (without fully disintegrating) by the time it reaches the ileum to allow the 25-hydroxyvitamin $D_2$ and/or 25-hydroxyvitamin $D_3$ to diffuse slowly from the wax matrix into the contents of the lower small intestine.

Examples of other lipid matrices that may be of value are glycerides, fatty acids and alcohols, and fatty acid esters.

Another suitable controlled-release oral drug delivery system is the Eudragit RL/RS system in which the active ingredient, 25-hydroxyvitamin $D_2$ and/or 25-hydroxyvitamin $D_3$, is formed into granules having a dimension of 25/30 mesh. The granules are then uniformly coated with a thin polymeric lacquer which is water insoluble but slowly water permeable. The coated granules can be mixed with optional additives such as antioxidants, stabilizers, binders, lubricants, processing aids and the like. The mixture may be compacted into a tablet which, prior to use, is hard and dry and can be further coated, or it may be poured into a capsule. After the tablet or capsule is swallowed and comes into contact with the aqueous intestinal fluids, the thin lacquer begins to swell and slowly allows permeation by intestinal fluids. As the intestinal fluid slowly permeates the lacquer coating, the contained 25-hydroxyvitamin $D_2$ and/or 25-hydroxyvitamin $D_3$ is slowly released. By the time the tablet or capsule has passed through the small intestine, about four to eight hours or more later, the 25-hydroxyvitamin $D_2$/25-hydroxyvitamin $D_3$ will have been slowly but completely released. Accordingly, the ingested tablet will release a stream of 25-hydroxyvitamin $D_2$ and/or 25-hydroxyvitamin $D_3$ as well as any other active ingredient.

The Eudragit system is comprised of high permeability lacquers (RL) and low permeability lacquers (RS). RS is a water insoluble film former based on neutral swellable methacrylic acids esters with a small proportion of trimethylammonioethyl methacrylate chlorides, the molar ratio of the quaternary ammonium groups to the neutral ester group is about 1:40. RL is also a water insoluble swellable film former based on neutral methacrylic acid esters with a small portion of trimethylammonioethyl methacrylate chloride, the molar ratio of quaternary ammonium groups to neutral ester groups is about 1:20. The permeability of the coating and thus the time course of drug release can be titrated by varying the proportion of RS to RL coating material. For further details of the Eudragit RL/RS system, reference is made to technical publications available from Rohm Tech, Inc. 195 Canal Street, Maiden, Mass., 02146. See also, K. Lehmann, D. Dreher "Coating of tablets and small particles with acrylic resins by fluid bed technology", *Int. J. Pharm. Tech. & Prod. Mfr.* 2(r), 31-43 (1981), incorporated herein by reference.

Other examples of insoluble polymers include polyvinyl esters, polyvinyl acetals, polyacrylic acid esters, butadiene styrene copolymers and the like, Once the coated granules are either formed into a tablet or put into a capsule, the tablet or capsule is coated with an enteric-coating material which dissolves at a pH of 7.0 to 8.0. One such pH dependent enteric-coating material is Eudragit L/S which dissolves in intestinal fluid but not in the gastric juices. Other enteric-coating materials may be used such as cellulose acetate phthalate (CAP) which is resistant to dissolution by gastric juices but readily disintegrates due to the hydrolytic effect of the intestinal esterases.

The particular choice of enteric-coating material and controlled release coating material must provide a controlled and substantially constant release over a period of 4 to 8 hours or more so that release is delayed until the formulation reaches the ileum. Moreover, the controlled release composition in accordance with the present invention, when administered once a day, suitably provides substantially constant intralumenal, intracellular and blood 25-hydroxyvitamin D levels compared to an equal dose of an immediate release composition of 25-hydroxyvitamin $D_2$/25-hydroxyvitamin $D_3$ administered once a day In another embodiment of the invention, sterile, isotonic formulations of 25-hydroxyvitamin $D_2$, 25-hydroxyvitamin $D_3$ or combinations thereof may be prepared which are suitable for gradual intravenous administration. Such formulations are prepared by dissolving 25-hydroxyvitamin $D_2$ and/or 25-hydroxyvitamin $D_3$ in absolute ethanol, propylene glycol or other suitable solvents, and combining the resulting solutions with surfactants, salts and preservatives in appropriate volumes of water for injection. Such formulations can be administered slowly from syringes via heparin locks or by addition to larger volumes of sterile solutions (e.g., saline solution) being steadily infused over time.

The dosage forms may also contain adjuvants, such as preserving or stabilizing adjuvants. They may also contain other therapeutically valuable substances or may contain more than one of the compounds specified herein and in the claims in admixture.

Advantageously, 25-hydroxyvitamin $D_2$, 25-hydroxyvitamin $D_3$ or combinations thereof together with other therapeutic agents can be orally or intravenously administered in accordance with the above described embodiments in dosage amounts of from 1 to 100 mcg per day, with the preferred dosage amounts of from 5 to 50 mcg per day. If the compounds of the present invention are administered in combination with other therapeutic agents, the proportions of each of the compounds in the combination being administered will be dependent on the particular disease state being addressed. For example, one may choose to orally administer 25-hydroxyvitamin $D_2$ and/or 25-hydroxyvitamin $D_3$ with one or more calcium salts (intended as a calcium supplement or dietary phosphate binder), bisphosphonates, calcimimetics, nicotinic acid, iron, phosphate binders, cholecalciferol, ergocalciferol, active Vitamin D sterols, glycemic and hypertension control agents, and various antineoplastic agents. In addition, one may choose to intravenously administer 25-hydroxyvitamin $D_2$ and/or 25-hydroxyvitamin $D_3$ with cholecalciferol, ergocalciferol, active Vitamin D sterols, glycemic and hypertension control agents, and various antineoplastic agents. In practice, higher doses of the compounds of the present invention are used where therapeutic treatment of a disease state is the desired end, while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

The inclusion of a combination of 25-hydroxyvitamin $D_3$ and 25-hydroxyvitamin $D_2$ in the described delivery systems allows the resulting formulations to be useful in supporting both the Vitamin $D_3$ and Vitamin $D_2$ endocrine systems. Currently available oral Vitamin D supplements and the previously marketed oral formulation of 25-hydroxyvitamin $D_3$ have supported just one or the other system.

The present invention is further explained by the following examples which should not be construed by way of limiting the scope of the present invention.

Example 1

One Embodiment of a Controlled Release Formulation for Oral Administration

Purified yellow beeswax and fractionated coconut oil are combined in a ratio of 1:1 and heated with continuous mixing to 75 degrees Celsius until a uniform mixture is obtained. The wax mixture is continuously homogenized while cooled to approximately 45 degrees Celsius. 25-hydroxyvitamin $D_2$ and 25-hydroxyvitamin $D_3$, in a ratio of 1:1, are dissolved in absolute ethanol and the ethanolic solution is added, with continuous homogenization, to the molten wax mixture. The amount of ethanol added is in the range of 1 to 2 v/v %. Mixing is continued until the mixture is uniform. The uniform mixture is loaded into soft gelatin capsules. The capsules are immediately rinsed to remove any processing lubricant(s) and briefly immersed in an aqueous solution of acetaldehyde in order to crosslink the gelatin shell. The concentration of the acetaldehyde solution and the immersion time is selected to achieve crosslinking to the desired degree, as determined by near-infrared spectrophotometry. The finished capsules are washed, dried and packaged.

Example 2

One Embodiment of a Formulation for Gradual Intravenous Administration

TWEEN Polysorbate 20 is warmed to approximately 50 to 60° F. (10 to 16° C.), and 25-hydroxyvitamin $D_3$, dissolved in a minimal volume of absolute ethanol, is added with continuous stirring. The resulting uniform solution of 25-hydroxyvitamin $D_3$, absolute ethanol and TWEEN Polysorbate 20 is transferred to a suitable volume of water for injection, which has been thoroughly sparged with nitrogen to remove all dissolved oxygen. Sodium chloride, sodium ascorbate, sodium phosphate (dibasic and monobasic), and disodium edetate are added, followed by sufficient stirring under a protective nitrogen atmosphere, to produce an isotonic homogeneous mixture containing, per 2 mL unit volume: 20 mcg of 25-hydroxyvitamin $D_3$; <0.01% absolute ethanol; 0.40% (w/v) TWEEN Polysorbate 20; 0.15% (w/v) sodium chloride; 1.00% (w/v) sodium ascorbate; 0.75% (w/v) sodium phosphate dibasic anhydrous; 0.18% (w/v) sodium phosphate monobasic monohydrate; and, 0.11% (w/v) disodium edetate. This mixture is sterilized by filtration and filled, with suitable protection from oxygen contamination, into amber glass ampules having an oxygen headspace of less than 1%.

Example 3

Pharmacokinetics Testing in Dogs

Twenty male beagle dogs are divided randomly into two comparable groups and receive no supplemental Vitamin D for the next 30 days. At the end of this time, each dog in Group #1 receives a single soft gelatin capsule containing 25 mcg of 25-hydroxyvitamin $D_2$ prepared in a controlled release formulation similar to the one disclosed in Example 1. Each dog in the other group (Group #2) receives a single immediate-release soft gelatin capsule containing 25 mcg of 25-hydroxyvitamin $D_2$ dissolved in medium chain triglyceride oil. All dogs have received no food for at least 8 hours prior to dosing. Blood is drawn from each dog at 0, 0.5, 1, 1.5, 2, 3, 4, 6, 9, 15, 24, 36, and 72 hours after dose administration. The collected blood is analyzed for the contained levels of 25-hydroxyvitamin D, and the data are analyzed by treatment group. Dogs in Group #1 show a slower rise and a lower maximum (C max) in mean blood levels of 25-hydroxyvitamin D than dogs in Group #2. However, dogs in Group #1 show a more prolonged elevation of mean blood levels of 25-hydroxyvitamin $D_2$ relative to dogs in Group #2, despite the fact that the $C_{max}$ recorded in Group #1 is lower. The mean area under the curve (AUC), corrected for predose background levels (recorded at t=0), is substantially greater for Group #1 for 25-hydroxyvitamin D. These procedures demonstrate that administration of 25-hydroxyvitamin $D_2$ in the formulation described in this invention to dogs results in blood levels of 25-hydroxyvitamin D which rise much more gradually and remain more stable than after dosing with the same amount of 25-hydroxyvitamin $D_2$ formulated for immediate release (in medium chain triglyceride oil). The greater AUC calculated for blood levels of 25-hydroxyvitamin D in Group #1 demonstrates that the bioavailability of 25-hydroxyvitamin $D_2$ formulated as described herein is markedly improved.

Example 4

Pharmacokinetics Testing in Healthy Normal Volunteers

Sixteen healthy non-obese adults, aged 18 to 24 years, participate in an 11-week pharmacokinetic study in which they receive successively, and in a double-blinded fashion, two formulations of 25-hydroxyvitamin $D_2$. One of the formulations (Formulation #1) is a soft gelatin capsule containing 100 mcg of 25-hydroxyvitamin $D_2$ prepared in a controlled release formulation similar to the one disclosed in Example 1. The other formulation (Formulation #2) is an immediate-release soft gelatin capsule of identical appearance containing 100 mcg of 25-hydroxyvitamin $D_2$ dissolved in medium chain triglyceride oil. For 60 days prior to study start and continuing through study termination, the subjects abstain from taking other Vitamin D supplements. On Days 1, 3 and 5 of the study, all subjects provide fasting morning blood samples to establish pre-treatment baseline values. On the morning of Day 8, the subjects provide an additional fasting blood sample (t=0), are randomly assigned to one of two treatment groups. Both groups are dosed with a single test capsule prior to eating breakfast: one group receives a capsule of Formulation #1 and the other group receives a capsule of Formulation #2. Blood is drawn from each subject at 0.5, 1, 1.5, 2, 3, 4, 6, 8, 10, 12, 15, 24, 36, 48, 72 and 108 hours after dose administration. On the morning of Day 70, the subjects provide additional fasting morning blood samples (t=0) and are dosed with a single capsule of the other test formulation prior to eating breakfast. Blood is again drawn from each subject at 0.5, 1, 1.5, 2, 3, 4, 6, 8, 10, 12, 15, 24, 36, 48, 72 and 108 hours after dose administration. All collected blood is analyzed for the contained levels of 25-hydroxyvitamin D, and the data are analyzed by treatment formulation after correction for baseline content. Formulation #1 is found to produce a slower rise and a lower $C_{max}$ in mean blood levels of 25-hydroxyvitamin D than Formulation #2. However, Formulation #1 also produces a more prolonged elevation of mean blood levels of 25-hydroxyvitamin $D_2$ relative to Formulation #2, despite the fact that the recorded $C_{max}$ is lower. The mean AUC is substantially greater after administration of Formulation #1 for 25-hydroxyvitamin D. These procedures demonstrate that administration of 25-hydroxyvitamin $D_2$ in the formulation described in this invention to healthy human adults results in blood levels of 25-hydroxyvitamin D which rise much more gradually and remain more stable than after dosing with the same amount of 25-hydroxyvitamin $D_2$ formulated for immediate release (in medium chain triglyceride oil). The greater AUC calculated for blood levels of 25-hydroxyvitamin D after dosing with Formulation #1 demonstrates that the bioavailability of 25-hydroxyvitamin $D_2$ formulated as described herein is better.

Example 5

Efficacy Study in Healthy Adult Male Volunteers with Vitamin D Insufficiency

The effectiveness of three different formulations of Vitamin D in restoring serum 25-hydroxyvitamin D to optimal levels (>30 ng/mL) is examined in a 23-day study of healthy non-obese men diagnosed with Vitamin D insufficiency. One of the formulations (Formulation #1) is a soft gelatin capsule containing 30 mcg of 25-hydroxyvitamin $D_3$ prepared as illustrated in this invention. The second formulation (Formulation #2) is an immediate-release soft gelatin capsule of identical appearance containing 50,000 IU of ergocalciferol dissolved in medium chain triglyceride oil. The third formulation (Formulation #3) is an immediate-release soft gelatin capsule, also of identical appearance, containing 50,000 IU of cholecalciferol dissolved in medium chain triglyceride oil. A total of 100 healthy Caucasian and African-American men participate in this study, all of whom are aged 30 to 45 years and have serum 25-hydroxyvitamin D levels between 15 and 29 ng/mL (inclusive). All subjects abstain from taking other Vitamin D supplements for 60 days before study start and continuing through study termination, and from significant sun exposure. On Day 1 and 2 of the study, all subjects provide fasting morning blood samples to establish pre-treatment baseline values of serum 25-hydroxyvitamin D. On the morning of Day 3, the subjects provide an additional fasting blood sample (t=0), are randomly assigned to one of four treatment groups, and are dosed with a single test capsule prior to eating breakfast: the subjects in Group #1 each receive a single capsule of Formulation #1, and the subjects in Groups #2 and #3 each receive a single capsule of Formulation #2 or Formulation #3, respectively. Subjects in Group #4 receive a matching placebo capsule. Subjects in Group #1 each receive an additional capsule of Formulation #1 on the mornings of Days 4 through 22 before breakfast, but subjects in Groups #2, #3 and #4 receive no additional capsules. A fasting morning blood sample is drawn from each subject, irrespective of treatment group, on Days 4, 5, 6, 10, 17 and 23 (or 1, 2, 3, 7, 14 and 20 days after the start of dosing). All collected blood is analyzed for the contained levels of 25-hydroxyvitamin D, and the data are analyzed by treatment group after correction for baseline values. Subjects in all four treatment groups exhibit mean baseline serum 25-hydroxyvitamin D levels of approximately 16 to 18 ng/mL, based on analysis of fasting blood samples drawn on Days 1 through 3. Subjects in Group #4 (control group) show no significant changes in mean serum 25-hydroxyvitamin D over the course of the study. Subjects in Group #1 show a steadily increasing mean serum 25-hydroxyvitamin D reaching at least 30 ng/mL by Day 23. In marked contrast, subjects in Group #2 exhibit marked increases in mean serum 25-hydroxyvitamin D for the first few days post-dosing, reaching a maximum of just above 25 ng/mL, and then rapidly declining thereafter. By study end, serum 25-hydroxyvitamin D is significantly lower than baseline in Group #2. Subjects in Group #3 exhibit continuing increases in mean serum 25-hydroxyvitamin D through the first 2 weeks after dosing with gradual, but progressive, decreases occurring thereafter. By study end, mean serum 25-hydroxyvitamin D is below 30 ng/mL, being only approximately 11 ng/mL higher than pre-treatment baseline. The data from this study demonstrate that administration of 600 mcg of 25-hydroxyvitamin $D_3$, formulated as described herein and administered at a dose of 30 mcg per day for 20 days, is substantially more effective in restoring low serum levels of 25-hydroxyvitamin D to optimal levels than immediate-release formulations of 50,000 IU of either ergocalciferol or cholecalciferol administered in single doses, as currently recommended by the NKF and other leading experts on oral Vitamin D replacement therapy.

Example 6

Efficacy and Safety Study in End-Stage Renal Disease Patients Exhibiting Vitamin D Deficiency The efficacy and safety of intravenous 25-hydroxyvitamin $D_3$ in restoring serum 25-hydroxyvitamin D to optimal levels (>30 ng/mL) are examined in a 3-month study of patients with end-stage renal disease (ESRD) requiring regular hemodialysis and diagnosed with Vitamin D insufficiency. The formulation examined in this study is an aqueous isotonic and sterile solution containing 20 mcg of 25-hydroxyvitamin $D_3$ similar to the one disclosed in Example 2. A total of 50 healthy Caucasian, Asian, Hispanic and African-American subjects participate in this study, all of whom are at least 4-months on regular hemodialysis and have serum 25-hydroxyvitamin D levels below 15 ng/mL. Prior to enrolling, all subjects provide two fasting morning blood samples, separated by at least one week, to establish pre-treatment baseline values of serum calcium, plasma intact PTH, and serum 25-hydroxyvitamin D. On the morning of Day 1, the subjects are randomly assigned to one of two treatment groups, and they begin thrice weekly dosing with the test preparation, or with a matching placebo. All dosing occurs during regularly scheduled hemodialysis sessions and is accomplished by gradual injection (over a period of 1 to 5 minutes) into the blood exiting from the hemodialysis machine. Additional fasting blood samples and 24-hour urine collections are obtained from each subject at quarterly intervals for determination of serum calcium, plasma intact PTH and serum 25-hydroxyvitamin D. Throughout the study, all subjects adhere to a daily intake of approximately 1,000 to 1,500 mg of elemental calcium (from self-selected diets and calcium supplements, as needed) under the ongoing guidance of a dietician. At the conclusion of the study, the laboratory data are analyzed by treatment group and by test formulation after appropriate correction for baseline values. Both groups have comparable mean baseline values for serum 25-hydroxyvitamin D (range: 10.7 to 11.9 ng/mL), plasma intact PTH (range: 45.3 to 52.1 pg/mL) and serum calcium (range: 8.72 to 9.31 mg/dL). No significant changes in any of the laboratory mean values are observed in the placebo (control) group over the course of the study. Subjects in the treatment group receiving 25-hydroxyvitamin $D_3$ exhibit progressively increasing serum 25-hydroxyvitamin D levels during the first 3 months of dosing, reaching steady state levels thereafter. Mean serum calcium increases significantly from baseline in the treatment group receiving 25-hydroxyvitamin $D_3$, and is significantly higher than those observed in the placebo group. Episodes of hypercalcemia, defined as serum calcium above 9.5 mg/dL, are infrequently observed in both treatment groups. Data from this study demonstrate that the intravenous formulation of 25-hydroxyvitamin $D_3$ is effective at increasing serum 25-hydroxyvitamin D without causing unacceptable side effects related to calcium and PTH metabolism.

All patents, publications and references cited herein are hereby fully incorporated by reference. In case of conflict between the present disclosure and incorporated patents, publications and references, the present disclosure should control.

Embodiments contemplated in view of the foregoing description include the following numbered paragraphs.

1. Aسustained release oral dosage formulation of 25-hydroxyvitamin $D_2$, 25-hydroxyvitamin $D_3$, or a combination of 25-hydroxyvitamin $D_2$ and 25-hydroxyvitamin $D_3$.

2. The sustained release oral dosage formulation of paragraph 1, wherein the formulation further provides delayed release of the 25-hydroxyvitamin $D_2$, 25-hydroxyvitamin $D_3$, or combination of 25-hydroxyvitamin $D_2$ and 25-hydroxyvitamin $D_3$ after ingestion of the formulation.

3. The sustained release oral dosage formulation of paragraph 2, wherein release is substantially delayed until the 25-hydroxyvitamin $D_2$, 25-hydroxyvitamin $D_3$, or combination of 25-hydroxyvitamin $D_2$ and 25-hydroxyvitamin $D_3$ reaches the ileum of the intestine.

4. The sustained release oral dosage formulation of any one of the preceding paragraphs, comprising the 25-hydroxyvitamin $D_2$, 25-hydroxyvitamin $D_3$, or combination of 25-hydroxyvitamin $D_2$ and 25-hydroxyvitamin $D_3$ dispersed within a wax matrix.

5. The sustained release oral dosage formulation of paragraph 4, wherein the wax matrix comprises a wax and an oil.

6. The sustained release oral dosage formulation of paragraph 4 or 5, further comprising a glyceride.

7. The sustained release oral dosage formulation of any one of paragraphs 4 to 6, further comprising a gelatin capsule, the wax matrix being disposed in the gelatin capsule.

8. The sustained release oral dosage formulation of paragraph 7, wherein the gelatin capsule is a hard gelatin capsule.

9. The sustained release oral dosage formulation of any one of the preceding paragraphs, wherein the formulation is semi-solid at body temperature.

10. The sustained release oral dosage formulation of any one of the preceding paragraphs, comprising 1 to 50 mcg per unit dose of the 25-hydroxyvitamin $D_2$, 25-hydroxyvitamin $D_3$, or combination of 25-hydroxyvitamin $D_2$ and 25-hydroxyvitamin $D_3$.

11. Theسustained release oral dosage formulation of any one of the preceding paragraphs, wherein the sustained release is effected over a period of at least four hours.

12. The sustained release oral dosage formulation of any one of the preceding paragraphs, comprising 25-hydroxyvitamin $D_3$.

13. A sustained release oral dosage formulation of 25-hydroxyvitamin $D_3$ dispersed within a wax matrix comprising a wax, an oil, and a glyceride, and disposed within a hard gelatin capsule.

14. A method of treating 25-hydroxyvitamin D insufficiency or deficiency in a patient comprising orally administering to the patient a delayed, sustained release formulation according to any one of the preceding paragraphs.

15. The method of paragraph 14, wherein the formulation is administered once a day, and provides substantially constant intralumenal, intracellular and blood 25-hydroxyvitamin D levels compared to an equal dose of an immediate release formulation administered once a day.

16. The method of paragraph 14, comprising administering 1 to 100 mcg per day of the 25-hydroxyvitamin $D_2$, 25-hydroxyvitamin $D_3$, or combination of 25-hydroxyvitamin $D_2$ and 25-hydroxyvitamin $D_3$.

17. The method of paragraph 14, wherein the administration provides reduced aberrations in PTH compared to an equal dose of an immediate release formulation.

What is claimed is:
1. A soft gelatin capsule dosage form, consisting of:
a) a soft gelatin shell optionally treated with a cross linking agent and which gradually dissolves after oral administration, and
b) a pharmaceutical composition disposed in the soft gelatin shell and consisting essentially of
(1) (a) an active ingredient selected from 25(OH) vitamin D
(b) a matrix material comprising one or more compounds in the group of a glyceride, a fatty acid, a fatty alcohol, and a fatty acid ester; and
(c) ethanol; or
(2) (a) an active ingredient selected from 25(OH) vitamin D;
(b) an insoluble polymer comprising one or more selected from the group of swellable methacrylic acid esters, polyvinyl esters, polyvinyl acetal esters, polyacrylic acid esters and butadiene styrene copolymers; and
(c) ethanol.

2. The dosage form of claim 1, wherein the pharmaceutical composition disposed in the soft gelatin shell consists essentially of
(1) (a) an active ingredient selected from 25(OH) vitamin D
(b) a matrix material consisting comprising one or more compounds in the group of a glyceride, a fatty acid, a fatty alcohol, and a fatty acid ester; and
(c) ethanol.

3. The dosage form of claim 2, wherein the matrix material consists essentially of one or more in the group of a glyceride, a fatty acid, a fatty alcohol, and a fatty acid ester.

4. The dosage form of claim 2, wherein the matrix material comprises a glyceride.

5. The dosage form of claim 2, wherein the matrix material comprises a fatty acid.

6. The dosage form of claim 2, wherein the matrix material comprises a fatty alcohol.

7. The dosage form of claim 2, wherein the matrix material comprises a fatty acid ester.

8. The dosage form of claim 2, wherein the matrix material comprises fractionated coconut oil.

9. The dosage form of claim 2, wherein the soft gelatin shell is treated with a cross linking agent.

10. The dosage form of claim 2, wherein the active ingredient comprises vitamin $D_3$.

11. The dosage form of claim 1, wherein the pharmaceutical composition disposed in the soft gelatin shell consists essentially of
(2) (a) an active ingredient selected from 25(OH) vitamin D;
  (b) an insoluble polymer comprising one or more selected from the group of swellable methacrylic acid esters, polyvinyl esters, polyvinyl acetal esters, polyacrylic acid esters and butadiene styrene copolymers; and
  (c) ethanol.

12. The dosage form of claim 11, wherein the insoluble polymer comprises a swellable methacrylic acid ester.

13. The dosage form of claim 11, wherein the insoluble polymer comprises a polyvinyl ester.

14. The dosage form of claim 11, wherein the insoluble polymer comprises a polyvinyl acetal ester.

15. The dosage form of claim 11, wherein the insoluble polymer comprises a polyacrylic acid ester.

16. The dosage form of claim 11, wherein the insoluble polymer comprises a butadiene styrene copolymer.

17. The dosage form of claim 11, wherein the soft gelatin shell is treated with a cross linking agent.

18. The dosage form of claim 11, wherein the active ingredient comprises Vitamin $D_3$.

19. A soft gelatin capsule dosage form, consisting of a soft gelatin shell optionally treated with a cross linking agent and which gradually dissolves after oral administration, and a pharmaceutical composition disposed in the soft gelatin shell and consisting essentially of 25(OH) vitamin $D_3$, a matrix material consisting of a fatty acid ester, and ethanol.

20. A soft gelatin capsule dosage form, consisting of a soft gelatin shell optionally treated with a cross linking agent and which gradually dissolves after oral administration, and a pharmaceutical composition disposed in the soft gelatin shell and consisting essentially of 25(OH) vitamin $D_3$, an insoluble polymer consisting essentially of swellable methacrylic acid esters, and ethanol.

* * * * *